US009068977B2

(12) United States Patent
McNaughton et al.

(10) Patent No.: US 9,068,977 B2
(45) Date of Patent: Jun. 30, 2015

(54) NON-LINEAR ROTATION RATES OF REMOTELY DRIVEN PARTICLES AND USES THEREOF

(75) Inventors: Brandon H. McNaughton, Ypsilanti, MI (US); Raoul Kopelman, Ann Arbor, MI (US); Ramon Torres-Isea, Ann Arbor, MI (US); Roy Clarke, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 174 days.

(21) Appl. No.: 12/043,481

(22) Filed: Mar. 6, 2008

(65) Prior Publication Data

US 2008/0220411 A1    Sep. 11, 2008

Related U.S. Application Data

(60) Provisional application No. 60/906,002, filed on Mar. 9, 2007.

(51) Int. Cl.
*G01N 33/553* (2006.01)
*G01N 33/543* (2006.01)
*G01N 33/569* (2006.01)

(52) U.S. Cl.
CPC .... *G01N 33/54313* (2013.01); *G01N 33/54326* (2013.01); *G01N 33/569* (2013.01)

(58) Field of Classification Search
None
See application file for complete search history.

(56) References Cited

U.S. PATENT DOCUMENTS

| 3,676,679 A | 7/1972 | Waters |
| 4,778,758 A | 10/1988 | Ericsson et al. |
| 5,171,534 A | 12/1992 | Smith et al. |
| 5,232,839 A | 8/1993 | Eden et al. |
| 5,252,493 A | 10/1993 | Fujiwara et al. |
| 5,293,210 A | 3/1994 | Berndt |
| 5,336,600 A | 8/1994 | Monget |
| 5,374,527 A | 12/1994 | Grossman |
| 5,434,056 A | 7/1995 | Monget et al. |
| 5,516,670 A | 5/1996 | Kuehnle et al. |
| 5,534,527 A | 7/1996 | Black et al. |
| 5,593,854 A | 1/1997 | Berndt |

(Continued)

FOREIGN PATENT DOCUMENTS

| WO | WO-00/67037 A2 | 11/2000 |
| WO | WO-01/14591 A1 | 3/2001 |

(Continued)

OTHER PUBLICATIONS

Astalan et al., Biomolecular reactions studied using changes in Brownian rotation dynamics of magnetic particles, 2004, Biosensors and Bioelectronics, 19: pp. 945-951.*

(Continued)

*Primary Examiner* — Chris L Chin
(74) *Attorney, Agent, or Firm* — Marshall, Gerstein & Borun LLP

(57) ABSTRACT

The present invention relates to biological sensors. In particular, the present invention relates to the use of remotely driven nonlinear rotation of particles (e.g., magnetic particles) for detection of cells such as microorganisms (e.g., bacteria and viruses). The present invention further relates to the use of remotely driven nonlinear rotation of particles for measurement of physical properties of a solution (e.g., viscosity).

31 Claims, 12 Drawing Sheets

(56) References Cited

U.S. PATENT DOCUMENTS

| | | | |
|---|---|---|---|
| 5,716,798 | A | 2/1998 | Monthony et al. |
| 5,770,388 | A | 6/1998 | Vorpahl |
| 5,770,440 | A | 6/1998 | Berndt |
| 5,814,474 | A | 9/1998 | Berndt |
| 5,888,760 | A | 3/1999 | Godsey et al. |
| 5,910,300 | A | 6/1999 | Tournier et al. |
| 5,998,224 | A | 12/1999 | Rohr et al. |
| 5,998,517 | A | 12/1999 | Gentle, Jr. et al. |
| 6,002,817 | A | 12/1999 | Kopelman et al. |
| 6,027,946 | A | 2/2000 | Weitschies et al. |
| 6,096,272 | A | 8/2000 | Clark et al. |
| 6,107,102 | A | 8/2000 | Ferrari |
| 6,143,558 | A | 11/2000 | Kopelman et al. |
| 6,159,686 | A | 12/2000 | Kardos et al. |
| 6,275,031 | B1 | 8/2001 | Simmonds |
| 6,372,485 | B1 | 4/2002 | Clark et al. |
| 6,395,506 | B1 | 5/2002 | Pitner et al. |
| 6,437,563 | B1 | 8/2002 | Simmonds et al. |
| 6,518,747 | B2 | 2/2003 | Sager et al. |
| 6,586,259 | B1 | 7/2003 | Mahan et al. |
| 6,596,532 | B1 | 7/2003 | Hyman et al. |
| 6,597,176 | B2 | 7/2003 | Simmonds et al. |
| 6,632,655 | B1 | 10/2003 | Mehta et al. |
| 6,660,381 | B2 | 12/2003 | Halas et al. |
| 6,777,226 | B2 | 8/2004 | Jeffrey et al. |
| 6,780,581 | B2 | 8/2004 | Vesey et al. |
| 6,825,655 | B2 | 11/2004 | Minchole et al. |
| 6,900,030 | B2 | 5/2005 | Pitner et al. |
| 6,927,570 | B2 | 8/2005 | Simmonds et al. |
| 7,115,384 | B2 | 10/2006 | Clark et al. |
| 7,183,073 | B2 | 2/2007 | Hyman et al. |
| 7,323,139 | B2 | 1/2008 | LaBorde et al. |
| 7,341,841 | B2 | 3/2008 | Metzger et al. |
| 7,547,554 | B2 | 6/2009 | Odefey |
| 7,564,245 | B2 | 7/2009 | Lee |
| 7,575,934 | B2 | 8/2009 | Atwood |
| 7,691,600 | B2 | 4/2010 | Mercader Badia et al. |
| 2002/0150914 | A1* | 10/2002 | Andersen et al. ............ 435/6 |
| 2003/0012693 | A1 | 1/2003 | Otillar et al. |
| 2003/0076087 | A1 | 4/2003 | Minchole et al. |
| 2003/0124516 | A1 | 7/2003 | Chung et al. |
| 2003/0169032 | A1 | 9/2003 | Minchole et al. |
| 2004/0033627 | A1 | 2/2004 | Aytur et al. |
| 2004/0058458 | A1 | 3/2004 | Anker et al. |
| 2005/0048672 | A1 | 3/2005 | Luxton et al. |
| 2006/0008924 | A1 | 1/2006 | Anker et al. |
| 2006/0057578 | A1 | 3/2006 | Willner et al. |
| 2006/0160171 | A1 | 7/2006 | Bachur et al. |
| 2006/0210987 | A1 | 9/2006 | Gleich |
| 2007/0020720 | A1 | 1/2007 | Colin et al. |
| 2007/0037225 | A1 | 2/2007 | Metzger et al. |
| 2007/0205767 | A1* | 9/2007 | Xu et al. ............ 324/304 |
| 2008/0038769 | A1 | 2/2008 | Bernardi et al. |
| 2008/0220411 | A1 | 9/2008 | McNaughton et al. |
| 2009/0085557 | A1 | 4/2009 | Krozer et al. |
| 2009/0136953 | A1 | 5/2009 | Gold et al. |
| 2009/0269854 | A1 | 10/2009 | Kageyama |
| 2010/0033158 | A1 | 2/2010 | Dittmer et al. |
| 2010/0068755 | A1 | 3/2010 | Walsh et al. |
| 2010/0072994 | A1 | 3/2010 | Lee et al. |
| 2010/0129857 | A1 | 5/2010 | Walsh et al. |

FOREIGN PATENT DOCUMENTS

| | | |
|---|---|---|
| WO | WO-03/019188 A1 | 3/2003 |
| WO | WO-2006/104700 A1 | 10/2006 |
| WO | WO-2007/120095 A1 | 10/2007 |
| WO | WO-2008/075285 A1 | 6/2008 |
| WO | WO-2009/037636 A1 | 3/2009 |
| WO | WO-2010/026551 A1 | 3/2010 |
| WO | WO-2010/041178 A1 | 4/2010 |
| WO | WO-2010/048511 A1 | 4/2010 |
| WO | WO-2011/021142 A1 | 2/2011 |
| WO | WO-2012/027747 A2 | 3/2012 |

OTHER PUBLICATIONS

Kurlyandskaya et al., Magnetic dynabeads detection by sensitive element based on giant magnetoimpedance, Jun. 2004, Biosensors and Bioelectronics, 20: pp. 1611-1616.*

Elfwing et al., "Observing Growth and Division of Large Numbers of Individual Bacteria by Image Analysis," Applied and Environmental Microbiology,( 2004) 70(2):675 678.

Haukanes et al, "Application of Magnetic Beads in Bioassays," Bio-Technology (1993) 11, 60.

Olsvik et al., "Magnetic Separation Techniques in Diagnostic Microbiology," Clinical Microbiology Reviews (1994) 7, 43.

Gu et al., "Using biofunctional magnetic nanoparticles to capture Gram-negative bacteria at an ultra-low concentration," Chemical Communications (2003) 15, 1966.

Rife et al., "Design and performance of GMR sensors for the detection of magnetic microbeads in biosensors," Sensors and Actuators A (2003) 107, 209.

Shen et al, "In situ detection of single micron-sized magnetic beads using magnetic tunnel junction sensors," Applied Physics Letters (2005) 86, 253901.

Anker et al, "Magnetically modulated optical nanoprobes," Applied Physics Letters (2003) 82, 1102.

Biswal et al, "Micromixing with Linked Chains of Paramagnetic Particles," Anal. Chem (2004) 76, 6448.

Korneva et al., "Carbon Nanotubes Loaded with Magnetic Particles," Nano Lett (2005) 5, 879.

McNaughton et al., "Sudden Breakdown in Linear Response of a Rotationally Driven Magnetic Microparticle and Application to Physical and Chemical Microsensing," Journal of Physical Chemistry B (2006) 110, 18958.

Petkus et al., "Detection of FITC-cortisol via Modulated Supraparticle Lighthouses," Anal. Chem (2006) 78, 1405.

Behrend et al., "Microrheology with modulated optical nanoprobes (MOONs)," Journal of Magnetism and Magnetic Materials (2005) 293, 663.

Zhao et al., "A rapid bioassay for single bacterial cell quantitation using bioconjugated nanoparticles," Proceedings of the National Academy of Sciences (2004) 101, 15027.

Shelton et al., "Nonlinear motion of optically torqued nanorods," Physical Review E (2005) 71, 36204.

Häfeli et al., "Characterization of Magnetic Particles and Microspheres and Their Magnetophoretic Mobility Using a Digital Microscopy Method," European Cells and Materials (2002) 3, 34.

Hulteen et al., "Nanosphere lithography: A materials general fabrication process for periodic particle array surfaces" J. Vac. Sci. Technol. A (1995) 13, 1553-1558.

Lu et al., "Nanophotonic Crescent Moon Structures with Sharp Edge for Ultrasensitive Biomolecular Detection by Local Electromagnetic Field Enhancement Effect," Nano Lett.(2005) 5, 119.

Jiang et al., "A Lost-Wax Approach to Monodisperse Colloids and Their Crystals," Science. 291:453-457, 2001.

Cebers et al, "Dynamics of an active magnetic particle in a rotating magnetic field," Physical Review E (2006) 73, 21505.

Valberg et al., "Magnetic Particle Motions Within Living Cells," Biophys. J. 1987, 52, 537.

Shankar et al., "Experimental determination of the kinematic viscosity of glycerol-water mixtures," Proc. R. Soc. Lond. A 1994, 444, 573.

Stober et al., "Controlled Growth of Monodisperse Silica Spheres in the Micron Size Range," Journal of Colloid and Interface Science 1968, 26, 62.

Nozawa et al, "Smart Control of Monodisperse Stolber Silica Particles: Effect of Reactant Addition Rate on Growth Process," Langmuir 2005, 21, 1516-1523.

Puig-De-Morales et al., "Measurement of cell microrheology by magnetic twisting cytometry with frequency domain demodulation," J Appl Physiol 2001, 91, 1152.

Newman et al, "Motions of a Magnetic Particle in a Viscous Medium," Journal of Applied Physics 39 (1968) 5566.

Gitterman et al., "Order and chaos: are they contradictory or complementary?," Eur. J. Phys. 23 (2002) 119-122.

(56) References Cited

OTHER PUBLICATIONS

Purcell et al., "Life at low Reynolds number," American Journal of Physics 45 (1977) 3-11.

Yamazaki et al., "Three-dimensional analysis of swimming properties of a spiral-type magnetic micro-machine," Sensors and Actuators A 105 (2003) 103-108.

Ishiyama et al., "Swimming of Magnetic Micro-Machines under a Very Wide-Range of Reynolds Number Conditions," IEEE Trans. Magn. (2001) 37.

McNaughton et al., "Fabrication of uniform half-shell magnetic nanoparticles and microspheres with applications as magnetically modulated optical nanoprobes," arXiv:cond-mat/0506418 (2005) (6 Pgs).

Connolly et al., "Experimental evaluation of the magnetic properties of commercially available magnetic microspheres," Bio-Medical Materials and Engineering 15 (2005) 421-431.

Waigh, "Microrheology of complex fluids," Rep. Prog. Phys. 68 (2005) 685-742.

Agayan et al., "Optical manipulation of metal-silica hybrid nanoparticles" Procedings of SPIE 5514 (2004) 502-513.

Merkt et al., "Capped colloids as light-mills in optical traps," arXiv:cond-mat/0605463 (2006) Submitted to: New J. Phys.

Ekinci et al., "Nanoelectromechanical systems," Review of Scientific Instruments 76 (2005) 061101.

Ilic et al., Journal of Vacuum Science & Technology B: Microelectronics and Nanometer Structures 19 (2001) 2825.

Ilic et al., "Virus detection using nanoelectromechanical devices," Appl. Phys. Lett. 85 (2004) 2604.

Verbridge et al., "High quality factor resonance at room temperature with nanostrings under high tensile stress," J. Appl. Phys. 99 (2006) 124304.

Bhiladvala et al., "Effect of fluids on the Q factor and resonance frequency of oscillating micrometer and nanometer scale beams," Physical Review E 69 (2004) 36307.

Paul et al., "Stochastic Dynamics of Nanoscale Mechanical Oscillators Immersed in a Viscous Fluid," Phys. Rev. Lett. 92 (2004) 235501.

Vignola et al., "Effect of viscous loss on mechanical resonators designed for mass detection," Applied Physics Letters 88 (2006) 041921.

Fennimore et al.,"Rotational actuators based on carbon nanotubes," Nat. 424 (2003) 408.

McNaughton et al. "Physiochemical microparticle sensors based on nonlinear magnetic oscillations." Sensors and Actuators B 121 p. 330-340. Oct. 20, 2006.

Bao et al., "Cell and Molecular Mechanics of Biological Materials," Nat. Mat., 2:715-725 (2003).

Behrend et al., "Brownian Modulated Optical Nanoprobes," Appl. Phys. Letts., 84:154-156 (2004).

Bornhop et al., "Advance in contrast agents, reporters, and detection," Journal of Biomedical Optics, 6(2):106-115 (2001).

Crick, "The Physical Properties of Cytoplasm. A Study by Means of the Magnetic Particle Method. Part II. Theoretical Treatment," Strangeways Research Laboratory, Cambridge, 505-532 (1950).

Crick, et al., "The Physical Properties of Cytoplasm A Study by Means of the Magnetic Particle Method—Part I Experimental," Strangeways Research Laboratory, 37-80 (1949).

Horvath et al., "Magnetic Dimer Motion Effects in a Rotating Magnetic Field (A Qualitative Model of Magnetoviscosity and Permittivity in Magnetorheological Suspensions)," Czech J. Phys., 43:671-681 (1993).

Jain, "Understanding barriers to drug delivery: high resolution in vivo imaging is key," Clinical Cancer Research, 5(7):1605-1606 (1999).

Kashevsky, "Nonlinear Flow-Particle Interaction in Suspensions of Fine Quasi-Rigid Ferroparticles: A Giant Magnetic Effect of Fluid Rotation," J. Phys. D: Appl. Phys., 34:518-524 (2001).

Kneipp et al., "Surface-Enhanced Raman Spectroscopy in Single Living Cells Using Gold Nanoparticles ," Applied Spectroscopy, 56(2):150-154 (2002).

Lapointe et al., "Static and Dynamic Properties of Magnetic Nanowires in Nematic Fluids," J. Appl. Phys., 97:10 (2005).

Mayer et al., "Measurement of the Fluorescence Lifetime in Scattering Media by Frequency-Domain Photon Migration ," Applied Optics, 38:4930-4938 (1999).

Metzger, "Amorphous Whiskers of a Cobalt-Gold Alloy," Nature, 212:176-177 (1966).

Moller et al., "Ultrafine particles cause cytoskeletal dysfunctions in macrophages," Toxicology and Applied Pharmacology, 182(3):197-207 (2002).

Nie et al., "Probing Single Molecules and Single Nanoparticles by Surface-Enhanced Raman Scattering," Science, 275(5303):1102-1106 (1997).

Richards-Kortum et al., "Quantitative Optical Spectroscopy for Tissue Diagnosis," Annual Review of Physical Chemistry, 47:555-606 (1996).

Shine et al., "The Rotation of a Suspended Axisymmetric Ellipsoid in a Magnetic Field," Rheol. Acta, 26:152-161 (1987).

Taylor et al., "Real-time molecular and cellular analysis: the new frontier of drug discovery," Current Opinion in Biotechnology, 12(1):75-81 (2001).

Wagnieres et al., "In vivo fluorescence spectroscopy and imaging for oncological applications," Photochemistry and Photobiology, 68(5):603-632 (1998).

Boucher et al., Bad bugs, no drugs: no ESKAPE! An update from the Infectious Diseases Society of America, Clin. Infect. Dis., 48(1):1-12 (2009).

Boucher et al., Epidemiology of methicillin-resistant Staphylococcus aureus, Clin. Infect. Dis., 46 Suppl 5:S344-9 (2008).

Chu et al., Staphylococcus aureus bacteremia in patients with prosthetic devices: costs and outcomes, Am. J. Med., 118(12):1416 (2005).

Deresinski, Counterpoint: Vancomycin and Staphylococcus aureus—an antibiotic enters obsolescence, Clin. Infest. Dis., 44(12):1543-8 (2007).

Elbez et al., Nanoparticle induced cell magneto-rotation: monitoring morphology, stress and drug sensitivity of a suspended single cancer cell, PLOS One, 6(12):e28475 (2011).

Fratamico et al., Detection of Escherichia coli 0157:H7 using a surface plasmon resonance biosensor, Biotechnology Techniques, 12(7):571-6 (1998).

Fujinami et al., Sensitive detection of bacteria and spores using a portable bioluminescence ATP measurement assay system distinguishing from white powder materials, J. Health Sci., 50:126-32 (2004).

Gfeller et al., Micromechanical oscillators as rapid biosensor for the detection of active growth of Escherichia coli, Biosens. Biolectron., 21(3):528-33 (2005).

Godin et al., Using buoyant mass to measure the growth of single cells, Nat. Methods, 7(5):387-90 (2010).

Ilic et al., Mechanical resonant immunospecific biological detector, Appl. Phys. Lett., 77:450-2 (2000).

Janssen et al., Controlled torque on superparamagnetic beads for functional biosensors, Biosens. Bioelectron., 24(7):1937-41 (2009).

Kinnunen et al., Monitoring the growth and drug susceptibility of individual bacteria using asynchronous magnetic bea rotation sensors, Biosensors and Bioelectronics, 26(5):2751-5 (2010).

Klevens et al., Changes in the epidemiology of methicillin-resistant Staphylococcus aureus in intensive care units in US hospitals, 1992-2003, Clin. Infest. Dis., 42(3):389-91 (2006).

Koskinen et al., Development of a rapid assay methodology for antimicrobial susceptibility testing of Staphylococcus aureus, Diagn. Microbiol. Infect. Dis., 62(3):306-16 (2008).

Kumar et al., Duration of hypotension before initiation of effective antimicrobial therapy is the critical determinant of survival in human septic shock, Crit. Care Med., 34(6):1589-96 (2006).

MacDougall et al., Antimicrobial stewardship programs in health care systems, Clin. Microbiol. Rev., 18(4):638-56 (2005).

McNaughton et al., Compact sensor for measuring nonlinear rotational dynamics of driven magnetic microspheres with biomedical applications, JMMM, 321:1648-52 (2009).

(56) References Cited

OTHER PUBLICATIONS

McNaughton et al., Single bacterial cell detection with nonlinear rotation rate shifts of driven magnetic microspheres, Appl. Phys. Lett., 91:224105 (2007).

Melle et al., Structure and dynamics of magnetorheological fluids in rotating magnetic fields, Phys. Rev. E, 61(4):4111-7 (2000).

National Nosocomial Infections Surveillance System, National Nosocomial Infections Surveillance (NNIS) System Report, data summary from Jan. 1992 through Jun. 2004, issued Oct. 2004, Am. J. Infect. Control., 32(8):470-85 (2004).

Noskin et al., National trends in *Staphylococcus aureus* infection rates: impact on economic burden and mortality over a 6-year period (1998-2003), Clin. Infect. Dis., 45(9):1132-40 (2007).

Sakoulas et al., Relationship of MIC and bactericidal activity to efficacy of vancomycin for treatment of methicillin-resistant *Staphylococcus aureus* bacteremia, J. Clin. Microbiol., 42(6):2398-402 (2004).

Spellberg et al., Trends in antimicrobial drug development: implications for the future, Clin. Infect. Dis., 38(9):1279-86 (2004).

Su et al., A self-assembled monolayer-based piezoelectric immunosensor for rapid detection of *Escherichia coli* O157:H7, Biosens. Bioelectron., 19(6):563-74 (2004).

Talbot et al., Bad bugs need drugs: an update on the development pipeline from the Antimicrobial Availability Task Force of the Infectious Diseases Society of America, Clin. Infect. Dis., 42(5):657-68 (2006).

Tenover et al., The challenges of emerging infectious diseases. Development and spread of multiply-resistant bacterial pathogens, JAMA, 275(4):300-4 (1996).

Tiemersma et al., Methicillin-resistant *Staphylococcus aureus* in Europe, 1999-2002, Emerg. Infect. dis., 10(9):1627-34 (2004).

Varshney, Interdigitated array microelectrodes based impedance biosensors for detection of bacterial cells, Biosens. Bioelectron., 24(10):2951-60 (2009).

Witte et al., Changing pattern of antibiotic resistance in methicillin-resistant *Staphylococcus aureus* from German hospitals, Infect. Control Hosp. Epidemiol., 22(11):683-6 (2001).

Witte, Antibiotic resistance in gram-positive bacteria: epidemiological aspects, J. Antimicrob. Chemother., 44 Suppl A:1-9 (1999).

Yang et al., Interdigitated Array microelectrode-based electrochemical impedance immunosensor for detection of *Escherichia coli* 0157:H7, Anal. Chem., 76(4):1107-13 (2004).

\* cited by examiner (a)

(b)

(c)

NON-LINEAR ROTATION RATES OF REMOTELY DRIVEN PARTICLES AND USES THEREOF

This application claims priority to application Ser. No. 60/906,002, filed Mar. 9, 2007, which is herein incorporated by reference in its entirety.

This invention was made with government support under grant number 0455330 awarded by the National Science Foundation DMR. The Government has certain rights in the invention.

FIELD OF THE INVENTION

The present invention relates to biological sensors. In particular, the present invention relates to the use of remotely driven non-linear rotation of particles (e.g., magnetic particles) for detection of cells such as microorganisms (e.g., bacteria and viruses) or biological molecules. The present invention additionally relates to the use of remotely driven non-linear rotation of particles for the monitoring of cell (e.g., microorganism) growth. The present invention further relates to the use of remotely driven non-linear rotation of particles for measurement of physical properties of a solution (e.g., viscosity).

BACKGROUND

The need to have accurate and rapid antibiotic susceptibility techniques is becoming more urgent due to the increased resistance of bacteria to antibiotics. The resistance of bacteria to antibiotics has been referred to by the Centers for Disease Control and Prevention (CDC) as one of the world's most pressing health problems. Currently, out of 2 million people who get infections in the US each year, approximately 90,000 of deaths occur as a result of the bacterial infection and, of these cases, over 70 percent are resistant to one or more antimicrobials.

A developing technique in microbiology, with potential applications to antimicrobial susceptibility measurements, has been the study of cell properties on the single cell level. Performing measurements on a single microbe rather than millions offers the advantage of taking measurements that are obtained on the time scale of cell division. Some microscopy-based single cell techniques appear to be currently suitable for the study of cell growth (Elfwing et al., Applied and Environmental Microbiology, 70(2):675 678, 2004); however, the same technique has not been demonstrated as a sensor that can both detect pathogens and perform antimicrobial susceptibility measurements. Using microscopy techniques alone would be especially difficult, when attempting to detect and optically track the growth of a single bacteria. For example, when the size of the bacterium is small, such as Staphylococcus aureus, the growth would be more difficult to measure with standard microscopy techniques, because of its smaller size and near-spherical shape.

Rapidly determining an antibiotic that would work against an infection would save lives and limit improper antimicrobial therapy. Correctly diagnosing a bacterial infection and measuring its growth and susceptibility to antimicrobials on the time scale that a doctor would prescribe an antimicrobial, would aid in appropriate antimicrobial therapy. Appropriate therapy significantly reduces the risk of death and limits the exposure of resistant bacterial strains to multiple ineffective treatments of antibiotics, reducing the risk of the development of further resistance.

Indeed, the CDC suggests that one of the ways to prevent antimicrobial resistance is simply to properly diagnose and properly treat an infection. The development of new and stronger antibiotics alone will not remedy the dilemma of increasing antimicrobial resistance. Instead, there is a need in the art for both new antimicrobial developments and for applications of technologies that will allow doctors to determine appropriate antimicrobial therapy.

SUMMARY OF THE INVENTION

The present invention relates to biological sensors. In particular, the present invention relates to the use of remotely driven non-linear rotation of particles (e.g., magnetic particles) for detection of cells such as microorganisms (e.g., bacteria and viruses) or biological molecules. The present invention additionally relates to the use of remotely driven non-linear rotation of particles for the monitoring of cell (e.g., microorganism) growth. The present invention further relates to the use of remotely driven non-linear rotation of particles for measurement of physical properties of a solution (e.g., viscosity).

For example, in some embodiments, the present invention provides a method of detecting the presence of an analyte (e.g., a microorganism such as a bacteria or a virus or a cell) or a biological molecule (e.g., protein, nucleic acid, lipoprotein) in a sample, comprising: contacting a particle (e.g., a magnetic particle) with the sample; and measuring the non-linear rotation rate of the particle in the presence or absence of the sample. In some embodiments, the non-linear rotation rate is above the critical rotation rate calculated using the equation $\Omega_c = mB/\kappa\eta V$, where m is the magnetic moment, B is the external magnetic field, $\kappa$ is the shape factor, $\eta$ is the dynamic viscosity, and V is volume. In some embodiments, the particle further comprises a ligand (e.g., an antibody) that specifically binds to the microorganism. In preferred embodiments, a change in the non-linear rotation rate of the particle in the presence of the sample is indicative of the microorganism binding to the sample. In some embodiments, measuring the non-linear rotation rate of the particle comprises rotating the particle with a magnet and observing the particle with a microscope. In some embodiments, the method further comprises the step of contacting the sample with a label that binds to the cell or biological molecule and alters the rotation rate of the particle when bound.

The present invention further provides a system, comprising particles (e.g., magnetic or electrically polarized particles) configured to bind to an analyte (e.g., microorganism, cell or biological molecule) of interest; a means for rotating said particles (e.g., a rotating magnetic field device or an electrical rotation device) configured for rotating the particles at a rate sufficient for the particles to undergo non-linear rotation. In some embodiments, the rotating magnetic field device comprises two Helmholtz coils or a permanent magnet and a motor configured for rotation of the permanent magnet. In some embodiments, the system further comprises a substrate, wherein the particles are held in position by the substrate, and wherein the substrate is configured to hold the particles under conditions such that the particles can rotate. In some embodiments, the substrate comprises an array of particles in microwells, wherein the microwells are composed of a transparent material and the remainder of the substrate is composed of an opaque material.

In some embodiments, the substrate is part of a fluidic cell. In certain embodiments, the system further comprises a detection device configured for the measurement of the non-linear rotation rate of the particles. In some embodiments, the detection device comprises a microscope. In other embodiments, the detection device comprises a camera, diode, diode array, or CCD sensor. In some embodiments, the detection device comprises a light source (e.g., a laser, an LED, a xenon lamp, an incandescent light source, a gas discharge lamp, a fluorescent light source, an LED array, a diode-laser array, a light source for continuous illumination, a light source for pulsed source illumination, a light source for modulated illumination, a light source for white light illumination, or a light source for filtered light illumination). In some embodiments, the detection device measures the rotation rate passively (e.g., using a Hall sensor to measure magnetic fields).

In some further embodiments, the system further comprises a computer and software, wherein the software is configured for analysis of the non-linear rotation rate of the particles.

The present invention additionally provides a method, comprising contacting particles with a solution comprising cells (e.g., bacteria) under conditions such that the particles bind to the cells; measuring the non-linear rotation rate of the particles over time, wherein the non-linear rotation rate is altered in response to change in concentration (e.g., due to cell growth) of the cells in the solution over time. In some embodiments, the method further comprises the step of contacting the solution with a test compound (e.g., antibiotic) and measuring the growth of the cells over time in the presence of the test compound and the absence of the test compound.

In still further embodiments, the present invention provides methods of measuring a physical property of a solution (e.g. viscosity) comprising measuring the non-linear rotation rate of a particle in the solution; and calculating the viscosity of the solution from the non-linear rotation rate (e.g., using the equations described in Examples 2 and 3). For example, in some embodiments, calculating the viscosity of the solution comprises the use of the equation $$\Omega_c = \frac{mB}{\gamma} = \frac{mB}{\kappa \eta V},$$

wherein $\kappa$ is the shape factor, $\eta$ is the dynamic viscosity, $\Omega_c$ is the non-linear rotation rate and V is the particle volume.

In some embodiments, the invention provides methods of measuring changes in the physical properties of a solution (e.g. viscosity). In some embodiments, measurement of the nonlinear rotation rate allows for continuous monitoring of fluid samples, allowing for real-time measurement of the changes in a fluid.

DESCRIPTION OF THE DRAWINGS

FIG. 4a shows the rotational response of a single magnetic particle with one attached bacterium at various external driving frequencies, where the squares are data and the line is a theoretical fit for a particle with a bacterium attached (solid curve) and for one without (dashed curve). FIG. 4b shows the average nonlinear rotation frequency shift of 20 particles for single bacterium attachment. FIG. 4c shows the change in nonlinear rotation rate as single bacterial cells sequentially attached to a single magnetic particle. FIG. 4d shows the change in normalized period resulting from growth of attached bacteria in a Luria-Bertani growth media (squares).

FIG. 5a shows a schematic of the asynchronous (nonlinear) rotation changes that a magnetic microsphere undergoes when bound to a bacterium. FIG. 5b shows the power spectral density of a rotating magnetic microsphere dimer driven at 3.75 Hz, where 1, 2, 3, 4, and 8 bacterial cells were sequentially attached.

DEFINITIONS

Figure 1:
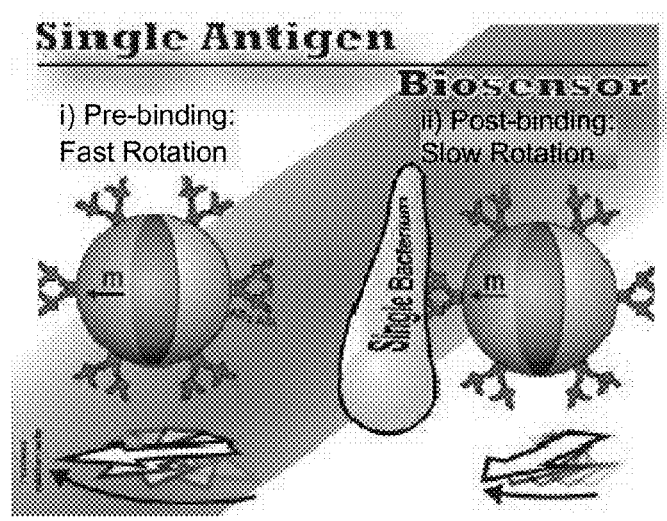
FIG. 1 shows a schematic of the nonlinear rotation rate changes that a magnetic microsphere undergoes when bound to a bacterium. The magnetic microsphere is functionalized with a secondary antibody (Ab2) and primary antibody (Ab1), where the secondary antibody used was goat anti-mouse IgG and the primary antibody used was mouse anti-*E. coli* IgG. The bottom of the figure shows fluorescent microscopy images of a rotating 2.0 µm magnetic microsphere with a single *Escherichia coli* bacterium attached. The dotted circle indicates the location of the magnetic microsphere.

To facilitate understanding of the invention, a number of terms are defined below.

As used herein, the term "non-linear rotation" refers to the effect that occurs to a rotating particle (e.g., magnetic particle) when the viscous torque that arises from rotational drag is comparable to the magnetic torque created by the external driving field. At low external driving frequencies, the magnetic particle rotates continuously and is synchronous with the external field, but at sufficiently high external driving frequencies, the particle becomes asynchronous with the driving field. In some embodiments, the external driving frequency, where the magnetic particle goes from linear to non-linear (synchronous to asynchronous) rotation, is dependent on environmental conditions in addition to the particle properties and is given by $$\Omega_c = mB/\kappa \eta V, \quad (1)$$

where m is the magnetic moment, B is the external magnetic field, $\kappa$ is the shape factor, $\eta$ is the dynamic viscosity, and V is volume.

As used herein, the term "MagMOON" refers to "magnetically modulated optical nanoprobes." MagMOONs are micro- and nano-particles that have optical properties (fluorescence excitation and emission spectra, fluorescence polarization, fluorescence lifetime and anisotropy, Raman spectra, and optical absorption, reflection, and scattering) that are modulated by magnetic field orientation or magnetic field gradient.

As used herein, the term "label" refers to any particle or molecule that can be used to provide a detectable (preferably quantifiable) effect. In some embodiments, labels utilized in the present invention detect a change in the, polarization, position, fluorescent, reflective, scattering or absorptive properties of the probes of the present invention. In some embodiments, the label comprises indicator dyes, enzymes, molecular recognition elements capable of synergistic sensing mechanisms and non-perturbative measurements, as well as fluorescent quantum dots and reflective gold and silver nanoparticles. In some embodiments, the label is integral to the probe. In other embodiments, it is attached to the surface of a probe (e.g., a "labeling particle"). In some embodiments, the label is an "indicator dye." In some embodiments, the label is a "molecular tag." In some embodiments, labels attach to the probes in the presence of analyte (e.g., fluorescently labeled antibodies attach to the probes in the presence of antigen bound to the probe). In some embodiments, the label is a native intracellular Raman active molecule.

As used herein, the term "labeling particle" refers to a particle attached to a MagMOON or Brownian particles that serves as a label. The particle may be attached using any suitable method including, but not limited to, covalent attachment, adsorption, or embedded (e.g., "embedded sub-nanometer particles").

As used herein, the term "untethered probe" refers to a probe configured to be suspended in a sample and optically interrogated without physical links (e.g., wires or optical fibers) to the outside of the sample.

As used herein, the term "a sensing agent" refers to a label configured to produce a detectable response when exposed to an analyte in its environment.

As used herein, the term "indicator dye" refers to any dye that changes an optical characteristic in response to a concentration of analyte in its environment. Optical characteristics include, but are not limited to, fluorescence intensity, position of a spectral peak, fluorescence lifetime and anisotropy, fluorescence polarization, and Raman spectral shape and intensity. In some preferred embodiments, indicator dyes are fluorescence indicator dyes. The dyes may excite in the ultraviolet, visible, or infrared. The dyes may detect the analyte directly, or in combination with ionophores, enzymes, other fluorophores or fluorescence quenchers.

As used herein, the term "spectral intensity" refers to an optical signal at one or more than one spectral wavelength. Optical signals include but are not limited to fluorescence, absorbance, reflection, and Raman spectral signals.

As used herein, the term "magnetic probe" refers to any probe that is capable of being altered in a magnetic field. In some embodiments, the probes are permanently magnetized. In other embodiments, the probes are magnetized only in the presence of an external magnetic field.

As used herein, the term "magnetically modulated" refers to a signal that is controlled and changed by a changing magnetic field orientation or gradient. The invention is not limited by the modulation waveform. The magnetic field may rotate continuously in one direction, or alternate direction. It may rotate a complete circle, or a small angle. It may rotate at a constant rate, or a changing rate, or may rotate rapidly to a particular orientation, pause while data is collected, and then rotate rapidly to a new orientation.

As used herein, the term "orienting agent" refers to all means of physically altering a probe in order to allow the probe to be oriented in a magnetic field, including but not limited to, the use of magnetic probes, the embedding of magnetic material in a non-magnetic probe, or the vapor deposition of magnetic material onto probes.

As used herein, the term "a device configured for the detection of said labels" refers to any device suitable for detection of a signal from labels that are in communication with the magnetic probes of the present invention. In some embodiments, the device includes an orienting component configured to rotate the magnetic probes and a detection component configured to detect a signal from the label (e.g., a fluorescent indicator dye).

As used herein, the term "nanobottle shell" refers to a shell of material that is suitable for encapsulating a plurality of probes of the present invention. In preferred embodiments, the pores in the nanobottle allow for the flow of small molecule analytes, but do not allow for the flow of the probes. Nanobottles may be composed of any suitable material, including, but not limited to, those disclosed below.

As used herein, the term "gradient sensing probes" refers to probes that are sensitive to small changes in molecule tension. In some embodiments, gradient sensing probes contain FRET donor and acceptor molecules that provide a change in fluorescence signal in response to small changes in molecule (e.g., a DNA molecule) tension.

As used herein, the term "sub-nanometer particle" refers to a particle that is smaller than a nanometer in diameter and is capable of being embedded into a probe of the present invention (e.g., by rolling as disclosed herein).

As used herein, the term "instructions for using said probes to detect an analyte in a sample" includes instructions for using the probes contained in the kit for the detection of any suitable "analyte." In some embodiments, the instructions further comprise the statement of intended use required by the U.S. Food and Drug Administration (FDA) in labeling in vitro diagnostic products.

The phrase "exogenous cellular stimulus" means a stimulus exogenous to a cell that is capable of stimulating the cell. By "stimulating the cell" is meant that the status of the intracellular analytes of the cell is changed (e.g., the concentration is changed). Such stimuli include, but are not limited to a variety of noxious, pathogenic and trophic stimuli. In one embodiment, the stimulus is a toxic agent (or "toxicant"). In another embodiment, the toxic agent is a biological toxin.

As used herein, the term "biological macromolecule" refers to large molecules (e.g., polymers) typically found in living organisms. Examples include, but are not limited to, proteins, nucleic acids, lipids, and carbohydrates.

As used herein, the term "molecular recognition element" refers to any molecule or atom capable of detecting a "biological macromolecules" In some embodiments, molecular recognition elements detect biological macromolecules present in or attached to the surface of intact cells or tissue. In other embodiments, molecular recognition elements detect biological macromolecules in vitro. In some embodiments, molecular recognition elements are antibodies.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, $F(ab')_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin. When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The term "chemical reaction" means reactions involving chemical reactants, such as inorganic compounds.

The term "microorganism" as used herein means an organism too small to be observed with the unaided eye and includes, but is not limited to bacteria, viruses, protozoans, fungi, and ciliates.

The term "bacteria" refers to any bacterial species including eubacterial and archaebacterial species. Examples include, but are not limited to, *Escherichia coli, Salmonella typhimurium, Bacillus subtilis*, and various species within the genera *Pseudomonas, Streptomyces*, and *Staphylococcus*.

The term "virus" refers to obligate, ultramicroscopic, intracellular parasites incapable of autonomous replication (i.e., replication requires the use of the host cell's machinery).

A "solvent" is a liquid substance capable of dissolving or dispersing one or more other substances. It is not intended that the present invention be limited by the nature of the solvent used.

As used herein, the term "liposome" refers to artificially produced spherical lipid complexes that can be induced to segregate out of aqueous media. The terms "liposome" and "vesicle" are used interchangeably herein.

As used the term "absorption" refers, in one sense, to the absorption of light. Light is absorbed if it is not reflected from or transmitted through a sample. Samples that appear colored have selectively absorbed all wavelengths of white light except for those corresponding to the visible colors that are seen.

As used herein, the term "spectrum" refers to the distribution of electromagnetic energies arranged in order of wavelength.

As used the term "visible spectrum" refers to light radiation that contains wavelengths from approximately 360 nm to approximately 800 nm.

As used herein, the term "ultraviolet spectrum" refers to radiation with wavelengths less than that of visible light (i.e., less than approximately 360 nm) but greater than that of X-rays (i.e., greater than approximately 0.1 nm).

As used herein, the term "infrared spectrum" refers to radiation with wavelengths of greater than 800 nm.

As used herein, the term "analyte object" refers to an object within a sample that will induce an effective change in resistance to rotation for a particle upon binding to the particle. Examples include, but are not limited to viruses, eukaryotic cells, prokaryotic cells, fungus, subcellular organelles, cytoskeleton, macromolecules, and molecules (e.g., proteins or nucleic acids)."

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DESCRIPTION OF THE INVENTION

The present invention relates to biological sensors. In particular, the present invention relates to the use of remotely driven non-linear rotation of particles (e.g., magnetic particles) for detection of cells such as microorganisms (e.g., bacteria and viruses) or biological molecules. The present invention additionally relates to the use of remotely driven non-linear rotation of particles for the monitoring of cell (e.g., microorganism) growth. The present invention further relates to the use of remotely driven non-linear rotation of particles for measurement of physical properties of a solution (e.g., viscosity).

I. Non-Linear Rotation

In some embodiments, the present invention provides systems and methods of measuring changes in non-linear rotation rates in response to binding of cells (e.g., microorganisms) to particles (e.g., magnetic particles).

For example, in experiments conducted during the course of development of some embodiments of the present invention, a nonlinear magnetic micro-oscillator was used to detect a single bacterium in a fluidic environment. This technique, which was used to detect a single *Escherichia coli*, is based on the changes in the nonlinear rotation of a magnetic microsphere driven by an external magnetic field. The presence of one *Escherichia coli* bacterium on the surface of a 2.0 μm magnetic microsphere caused an easily measurable change (~400%) in the drag of the system and, therefore, in the nonlinear rotation rate. The measurement can be made by standard microscopy techniques and the observed average shift in the nonlinear rotation rate changed by a factor of 3.8.

Magnetic microspheres and nanoparticles have been used for a variety of medical applications and incorporated into various diagnostic techniques (Haukanes and Kvam, Bio-Technology 11, 60 (1993); Olsvik et al., Clinical Microbiology Reviews 7, 43 (1994); Gu et al., Chemical Communications 15, 1966 (2003)). While magnetic particles have proven to be extremely useful, they have been generally utilized in techniques that depend on the translational properties of magnetic particles, such as magnetic separation, giant magnetoresistive (GMR) sensors (Rife et al., Sensors and Actuators A 107, 209 (2003)), and magnetic tunnel junctions (MTJ) sensors (Shen, X. Liu, D. Mazumdar, and G. Xiao, Applied Physics Letters 86, 253901 (2005)). It is possible, through standard microscopy techniques, to monitor the rotational behavior of single magnetic particles or small chains of them (Anker and Kopelman, Applied Physics Letters 82, 1102 (2003); Biswal and Gast, Anal. Chem 76, 6448 (2004); Lapointe et al., Journal of Applied Physics 97, 10 (2005); Korneva et al., Nano Lett 5, 879 (2005); McNaughton et al., Journal of Physical Chemistry B 110, 18958 (2006) and below examples). These small magnetic systems have been utilized to improve immunoassays (Petkus et al., Anal. Chem 78, 1405 (2006)), to act as micro-mixers (Biswal and Gast, supra), study microrheology (LaPointe et al., supra; Behrend et al., Journal of Magnetism and Magnetic Materials 293, 663 (2005)) and even to reduce interfering background in fluorescent spectroscopy measurements (Anker and Kopelman, supra). While single bacteria have been detected in fluid using nanoparticles (Zhao et al., Proceedings of the National Academy of Sciences 101, 15027 (2004)), prior to the present invention, the dynamic detection of single microbiological agents using magnetic particles has not been reported. Experiments conducted during the course of development of some embodiments of the present invention demonstrate the measurement of a single bacterium using changes in the rotational frequency of a magnetic microsphere.

In some embodiments, the methods of the present invention are based on the nonlinear rotation that a magnetic microsphere undergoes when driven by a rotating magnetic field (McNaughton et al., Journal of Physical Chemistry B 110, 18958 (2006); McNaughton et al., Sensors and Actuators B 121, 330 (2007), each of which is herein incorporated by reference in its entirety for all uses and examples below). The effect occurs when the viscous torque that arises from rotational drag is comparable to the magnetic torque created by the external driving field. At low external driving frequencies, the magnetic particle rotates continuously and is synchronous with the external field, but at sufficiently high external driving frequencies, the particle becomes asynchronous with the driving field. The external driving frequency, where the magnetic particle goes from linear to nonlinear (synchronous to asynchronous) rotation, is dependent on environmental conditions in addition to the particle properties and is given by $$\Omega_c = mB/\kappa\eta V, \quad (1)$$

where m is the magnetic moment, B is the external magnetic field, $\kappa$ is the shape factor, $\eta$ is the dynamic viscosity, and V is volume. The rotational dynamics of an actively rotated magnetic particle are then given by $$\langle \dot{\theta} \rangle = \begin{cases} \Omega & \Omega < \Omega_c \\ \Omega - \sqrt{\Omega^2 - \Omega_c^2} & \Omega > \Omega_c \end{cases}, \quad (2)$$

where $\langle \dot{\theta} \rangle$ is the particle's average rotation rate and $\Omega$ is the driving frequency of an external magnetic field. Equation 2 holds for low Reynolds number environments (Re<<1) and for the system of the present invention, Re≈$10^{-6}$.

Nonlinear rotation occurs when $\Omega > \Omega_c$ (Shelton et al., Physical Review E 71, 36204 (2005)) and the frequency of nonlinear rotation is used in some embodiments of the present invention to detect single microbiological agents. The parameters that are important in biological detection are shape and volume because of the drag changes that occur when a bacteria binds to a microsphere. When a bacteria or other cells or non-cell analytes attaches to a nonlinear rotating magnetic microsphere, the volume and shape of the rotating system are drastically changed, which produces more drag and, therefore, the rotation rate slows considerably. This is shown schematically in FIG. 1. The technique is dynamic in the sense that a change in drag causes a direct change in the nonlinear rotation rate. Past measurements have shown that this technique can measure a change of drag caused by an attachment of a 1.0 pm particle to a 1.9 pm nonlinear rotating magnetic microsphere.

In some embodiments of the present invention, nonlinear rotating magnetic particles are used when a biological agent attaches to the magnetic particle, the nonlinear rotation frequency changes. This allows for single biological agent detection in fluidic environments.

Accordingly, in some embodiments, the present invention (See, Example 1), provides systems and methods that detect changes in the nonlinear rotation frequency of magnetic microparticles upon association of any analyte to the microparticle.

Accordingly, in some embodiments, the present invention provides methods of detecting the binding of microorganisms or other analytes to particles (e.g., magnetic particles). In some embodiments, the nonlinear rotation rate is assayed at a fixed external rotation rate (e.g., a rate at which the particle exhibits non-linear rotation behavior).

Figure 7:
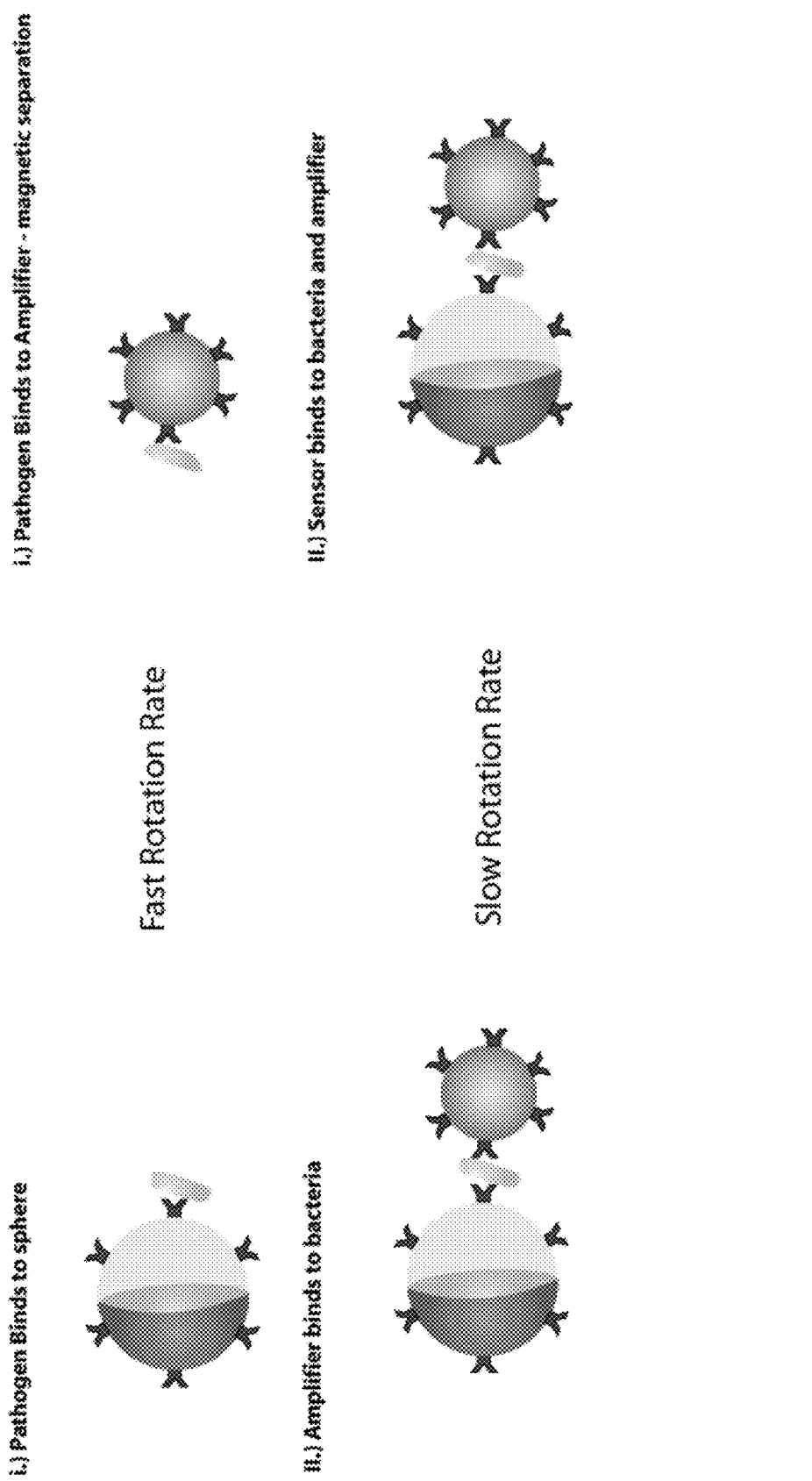
FIG. 7 shows a schematic of amplification through the use of a label.

In some embodiments (See e.g., FIG. 7), a "label" is used to amplify the change in the rotation rate. When a biological agent attaches to a rotating magnet it causes a change in drag. This change in drag can be amplified through the attachment of a sphere or some other body (label). In some embodiments, the amplification is large enough to cause a nonlinear rotating particle to go from linear to nonlinear (synchronous to asynchronous).

In some embodiments, the methods are carried out in the liquid phase. Detection of microorganism binding in the liquid phase allows for more efficient detection of microorganisms, which are commonly present in an aqueous environment.

The present invention is not limited to the detection of a particular analyte. In some embodiments, the analyte is a microorganism or other cell. For example, in some embodiments, bacteria are detected (e.g., bacteria in growth phase or spores). In other embodiments, viruses are detected. In some embodiments, the methods of the present invention are used to detect the presence of pathogenic microorganisms (e.g., in bodily fluids or secretions, in food products, or in environmental or clinical settings). In other embodiments, the systems and methods of embodiments of the present invention are used to detect eukaryotic cells (e.g., yeast cells, mammalian cells (e.g., cancer cells, stem cells), etc.). In still further embodiments, the systems and methods of embodiments of the present invention are used to detect proteins, nucleic acids, lipoproteins (e.g., LDL, HDL, VLDL, etc) or other biological molecules.

Figure 9:
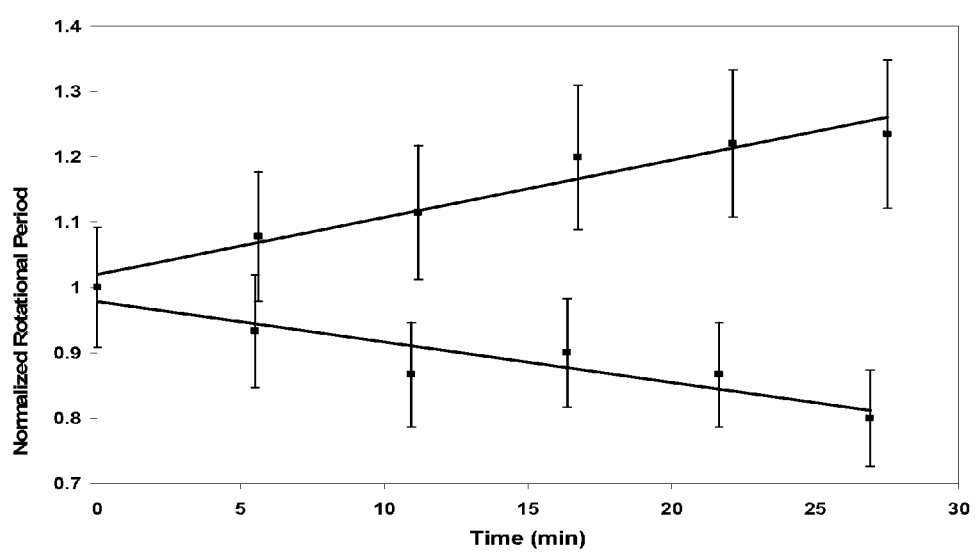
FIG. 9 shows the effect of antibiotic administration on growth of bacteria.

In other embodiments, the methods of the present invention are utilized to monitor the size change of an analyte in solution. In some embodiments, change in size is due to binding of an entity to an analyte (e.g., protein-protein interactions such as ligand binding or antibody antigen binding, nucleic acid-nucleic acid interactions, chemical modification, etc.). In other embodiments, change in size is due to growth of bacteria or other cells (e.g., yeast or mammalian (e.g., cancer) cells) in a solution. For example, in some embodiments, growth of bacteria in solution is monitored in the presence and absence of a test compound (e.g., antibiotic) and the effect of the test compound on rate of growth of the bacteria is monitored. FIG. 9 shows a measurement of the rate of growth or bacteria in the presence and absence of an antibiotic. In some embodiments, the rate of growth of bacteria is monitored by monitoring volume changes on the single cell level.

When an attached bacteria grows, the total drag that the system experiences is increased. This bacterial growth therefore causes a decrease in the nonlinear rotation rate and this can be used to approximate the size of the bacteria. The size of the rotating system as the bacteria grows can be calculated using the equation given by $$\kappa_2 V_2 = \kappa_1 V_1 \left[\frac{\langle \dot{\theta}_1 \rangle}{\langle \dot{\theta}_2 \rangle}\right]^{\frac{1}{2}} \left[\frac{2\Omega - \langle \dot{\theta}_1 \rangle}{2\Omega - \langle \dot{\theta}_2 \rangle}\right]^{\frac{1}{2}}, \quad (3)$$

where $\kappa_1$ and $\kappa_2$ are the shape factors before and after growth, $V_1$ and V2 are the volume of the rotating system before and after growth. For example, if the system under consideration is a single bacterium with attached nanoparticles that are much less than the size of the bacteria, then the length of a bacteria (e.g., a rod shaped bacteria) is determined by $$\ell = \frac{3\kappa_1 V_1}{4\pi w^2 \kappa_2} \left[\frac{\langle \dot{\theta}_1 \rangle}{\langle \dot{\theta}_2 \rangle}\right]^{\frac{1}{2}} \left[\frac{2\Omega - \langle \dot{\theta}_1 \rangle}{2\Omega - \langle \dot{\theta}_2 \rangle}\right]^{\frac{1}{2}}, \quad (4)$$

where w is the width of the bacteria and l is the length. Thus, a change in drag causes a direct change in the nonlinear rotation rate and the growth of an attached bacterium causes further changes in drag. It is in this way, through changes in drag, that single bacterial growth is monitored, allowing for rapid antimicrobial susceptibility measurements to be made.

In yet other embodiments, the systems and methods of the present invention are used to detect changes in viscosity of a solution. For example, in some embodiments, viscosity changes upon blood clotting, blood viscosity, food changes, or other changes in viscosity of solutions are measured.

In further embodiments, the system and methods of the present invention are used to monitor the response of biological molecules or cells to external stimulus (e.g., chemical agents such as antimicrobial agents or drugs, phase or gene therapy, radiation or chemotherapy).

II. Particles

In some embodiments, the present invention provides particles for the detection of analytes. In some embodiments, particles are magnetic particles. In some embodiments, the particles further comprise binding partners (e.g., antibodies) specific for the microorganism being detected. The present invention is not limited to magnetic particles. Any particle that can be rotated by an external rotation source may be utilized in the methods of the present invention. The below description provides exemplary particles and methods of generating them. One skilled in art recognizes that the particles of the present invention may be generated using any suitable method.

A. Particles

The particles of the present invention may be formulated of any suitable material. In some embodiments, probes include, but are not limited to, permanent magnetic probes, non-spherical opaque probes, polarized probes that rotate their polarization, and magnetophoretic probes that respond to field gradients not field direction. In some embodiments, the probes are smaller than 5 pm, and more preferably, smaller than 1 pm. Exemplary, non-limiting probes with magnetically controllable signal intensity are described below and in U.S Patent application 20040058458, which is herein incorporated by reference in its entirety.

i. Capped Permanent Magnet Probes

In some embodiments, permanent magnetic probes that blink once per revolution are produced by coating or capping one hemisphere of a magnetic particle with an opaque or reflective layer such as aluminum or gold.

For example, in some embodiments, a preferentially emitting particle is generated by vapor deposit of a thin layer of aluminum onto one side of the particle. The particles are generated by coating 4 μm polystyrene microspheres containing chromium dioxide (Spherotech) with vapor deposited aluminum and sputtered gold. The microspheres are magnetized so that their north side is uncoated. The aluminum absorbs or reflects light entering or exiting one hemisphere; the minimum thickness of aluminum that is opaque to visible light is around 20 nm. When in solution, the particles orient in an external magnetic field, and depending on their orientation, more or less light will reach the observer. By rotating the field, the particles are made to rotate, and appear to blink as the light emitting side comes in and out of view.

In some embodiments, a monolayer of particles is applied to a surface (e.g., a microscope slide) and left to dry. The microscope slide is then placed in a vapor deposition chamber in vacuum, and a thin layer of metal deposited on one side of the particles. The particles are then magnetized so that the capped side lies at a fixed angle to the magnetic dipole (e.g., the coated side is the magnetic south pole of the particle). The capped magnetic particles are then removed by sonication. In some embodiments, fluorescent particles are attached to the metal-capped magnetic particles. In other embodiments, fluorescent dye is embedded inside the magnetic particle itself.

In other embodiments, an opaque particle with a fluorescent surface is made to emit more from one hemisphere by bleaching or quenching dyes in the other hemisphere. For example, in some embodiments, a preferentially emitting particle is generated by bleaching the particle. Particles are deposited immobilized on a flat surface, and intense ultraviolet light shines on them to bleach fluorescent molecules in or on the particle. The side under the light will be bleached more rapidly than the other side that is shadowed by the particle. Magnetic material is usually opaque, so if there is enough magnetic material, the particle is expected to be opaque.

In other embodiments, non-magnetic particles are made magnetic by vapor depositing a magnetic material onto its surface. The procedure enables fine control over material composition and coating thickness. The half-shell particles produced are smoothly coated with controllable uniformity in amounts of magnetic material. The process is suitable for a wide range of particle sizes, shapes, and compositions, as well as for different material matrixes, providing a universal method of producing MagMOONs. Control over amount of deposited material solves the longstanding problem of creating magnetic micro and nanoparticles with uniform magnetic properties. Magnetic uniformity is especially important for single particle force and torque studies. A recent study of particles from 5 commercial companies demonstrated that the particles had variations in magnetic responsiveness varying between 30-80% from the average value (Häfeli et al., European Cells and Materials 3, 34 (2002)).

Different batches of MagMOONs coated with varying amounts of magnetic material have a different maximum rotation rate, and each batch can be differentiated based on rotation rate. This signal differentiation enables simultaneous measurements from different populations of MagMOONs that sense different analytes.

In some further embodiments, vapor deposition of magnetic materials onto microspheres and nanospheres provides a method for controlling the particle geometry and the resulting properties. Experiments conducted during the course of development of the present invention demonstrated that the coercivity of polycrystalline cobalt was enhanced by the presence of polystyrene nanospheres and arch-like structures formed on the surface of the spheres during deposition. It is contemplated that the presence of these arches affects the magnetic properties of the cobalt film. Additionally, the lightning rod effect creates large electromagnetic field enhancements at the tips with applications for SERS (surface enhanced Raman spectroscopy) and for non-linear optical effects, similar to enhancements seen with prism shaped particles (Hulteen et al., J. Vac. Sci. Technol. A 13, 1553-1558 (1995)) and nanocrescents (Lu et al., Nano Lett. 5, 119 (2005). In other embodiments, MOONs are produced by continuous deposition onto a reel tape coated with microspheres.

ii. Non-Spherical Probes

In other embodiments, probes are non-spherical probes. A rod shaped magnetic particle will automatically align with a strong magnetic field because of its shape; the magnetic material will make the probe somewhat opaque. Non-spherical probes have the added advantage over metal-capped probes that they can be separated from solution in strong magnetic fields without remagnetizing particles, or causing particles to aggregate. In some embodiments, probes are made more opaque by adding a strongly absorbing dye, or coating all or part of it with a thin layer of metal.

There are a number of ways of making non-spherical particles. For example, in some embodiments, particles are made in non-spherical molds (Jiang et al., Science. 291 :453-457). In other embodiments, particles are made by rolling between flat surfaces, or between two counter rotating cylinders. In still further embodiments, disk-shaped particles are made by crushing or rolling out already made particles In some embodiments, small fluorescent particles are imbedded into a magnetic particle, or alternatively, small magnetic particles are embedded into larger fluorescent particles iii. Chains In still further embodiments, chains of spherical MagMOONs are generated. These chains orient and blink the same way as other non-spherical probes. In some embodiments, chains of magnetic particles are spontaneously formed in a magnetic field. Such chains orient in the direction of the magnetic field. In other embodiments, permanently linked chains are generated by heating to above the glass transition state, applying a magnetic field, and then cooling.

In other embodiments, the chains are linked together only in the presence of chemical analyte, and the concentration of chains formed indicates the amount of analyte present. The amount of chain present is determined by any suitable method including, but not limited to, by measuring magnetically modulated fluorescence, transmission, or reflection.

vi. Labeling Particles

In some embodiments of the present invention, labels (e.g., fluorescent indicator dyes) are incorporated into the MagMOON itself. In other embodiments, the above-described MagMOONs are modified by the attachment of labeling particles (e.g., PEBBLES, See e.g., U.S. Pat. No. 6,143,558, herein incorporated by reference). In such embodiments, the label comes from labeling particles attached to, or embedded in, a MagMOON. Such a hybrid allows the advantages of sensing and detecting, while simplifying the production of the magnetically responsive optically modulated component of the MagMOON.

B. Labels

In some embodiments, the particles of the present invention further comprise a label for their detection or to monitor their rotation. In some embodiments, the label is an indicator dye. The present invention is not limited to a particular fluorescent dye. Any dye that fluoresces, including those that fluoresce in the UV and IR ranges of the spectrum, is contemplated by the present invention. Commercial sources for dyes include, but are not limited to, Molecular Probes (Eugene, Oreg.), Sigma/Aldrich (St. Louis, Mo.), Alfa Aesar (Ward Hill, Mass.), and Exciton (Dayton, Ohio).

In some embodiments, multiple dyes are used to generate ratiometric indicator dyes, which have two spectral peaks where the ratio of the two peak intensities depends on the chemical environment. For example, in some embodiments, one dye is responsive to the chemical concentration to be sensed, and the other emits a constant signal.

Dye properties such as excitation and emission spectral overlap with other dyes in the MagMOON, dynamic range, selectivity, photostability, quantum efficiency and cost are compared to find dyes best suited to the application. PEBBLEs enable use of dyes that would otherwise be toxic to cells, prevent interference from cellular proteins, and enable synergistic sensing mechanisms such as enzyme oxidation and ion correlation. MagMOONs further allow for the use of dyes that excite in the ultraviolet (where most dyes will excite, but autofluorescence is particularly problematic), and dyes with low quantum efficiency. In addition, spectral overlap is less of a concern because of multiplexing between distinguishable MagMOONs, and because a wider range of excitation wavelengths can be used The present invention is not limited to fluorescent labels. Any label that allows for the detection of particles oriented and moving in a magnetic field may be utilized. In other embodiments (e.g., RAMAN spectroscopy), the label is metal nanoparticles on the surface of the MagMOON. In other embodiments, metal coated MagMOONs are visualized using the methods of the present invention. In still further embodiments, detection utilizes dark-Field microscopy or a Superconducting Quantum Interference Device (SQUID) that measures the magnetization of rotating magnetic particles.

C. Nanobottles

In some embodiments, probes are encapsulated into nanobottles. A selectively porous polymer or lipid shell may be formed around any of the above particle types. Preferred shells for encapsulation are those that allow the particles to spin with a maximum rate dependent on the viscosity inside the shell, and independent of the environment outside the shell. In some embodiments, the shell is immobilized in a highly viscous environment, or attached to a rigid structure with antibodies, without preventing the internal particle from rotating in its compartment. It is preferable that the polymer shell be permeable to chemical species of interest, but impermeable to large proteins that may change the viscosity in the compartment unless interactions are desired for a particular type of analysis. The nanobottles of the present invention are particularly useful for detecting small intracellular molecules.

In some embodiments, the shell is a liposome. Liposomes form spontaneously when a lipid is hydrated in the presence of water, and if magnetic particles are present, then some of the lipids may form containing the particle. Liposomes can be easily modified to become porous. Alternatively, in other embodiments, shells are formed by coating a polymer (e.g., polystyrene) around an intermediary layer and dissolving the intermediary layer. In still further embodiments, magnetic particles are formed inside porous shell by precipitating iron oxide inside the shells. In yet other embodiments, the nanobottle comprises a sol-gel.

By varying the viscosity inside the compartment, particles are made with low viscosity that can spin rapidly in response to a rapidly rotating magnetic field (or oscillating field gradient), and particles with high viscosity compartments that respond only to more slowly changing fields (unless the viscosity outside is lower than inside and the whole nanobottle spins). Only the low viscosity particles can blink at high frequencies, whereas all particles can blink if the field changes slowly enough. Therefore, low and high viscosity particles are distinguished based on the maximum frequency that they will respond to for a given field strength.

In some embodiments, antibodies are attached to the outside of nanobottles, thus allowing targeting of the nanobottle to a specific cell, where the chemical sensor serves as a label. In other embodiments, oscillating magnetic filed gradients cause opaque magnetic particles within a nanobottle to move from one side of the capsule to the other, thereby masking and unmasking dye trapped within the particle, and causing the particle to blink.

D. Production of Particles

In some embodiments, particles (e.g., MagMOONs) are generated using a vapor deposition method. In some embodiments, MagMOONs are produced by coating a uniform half-shell of magnetic material (e.g., ferromagnetic cobalt) onto nanospheres and microspheres using ultra high vacuum (UHV) vapor deposition.

The use of top down deposition of magnetic materials solves the longstanding problem of non-uniformity in commercially made magnetic particles (usually produced using purely bottom up chemical synthesis). The control over material composition also increases the effective magnetic moment of the particles compared to iron oxide, and allows control over coercivity, With uniform magnetic particles, more accurate experiments can be designed, so as to better probe microrheology and molecular interactions. Additionally, this fabrication technique finds use in the modification of solid state sensors into MagMOONs, by the simple step of depositing a ferromagnetic metal onto the surface of a sensor.

III. Devices

In some embodiments, the present invention provides devices for use in monitoring changes in non-linear rotation rates of particles. In some embodiments, the devices comprise a means for orienting particles in a magnetic field. In some embodiments, the devices further comprise software for the analysis and presentation of the data. In some embodiments, the devices are compact and portable (e.g., portable immunoanalyzers).

Figure 3:
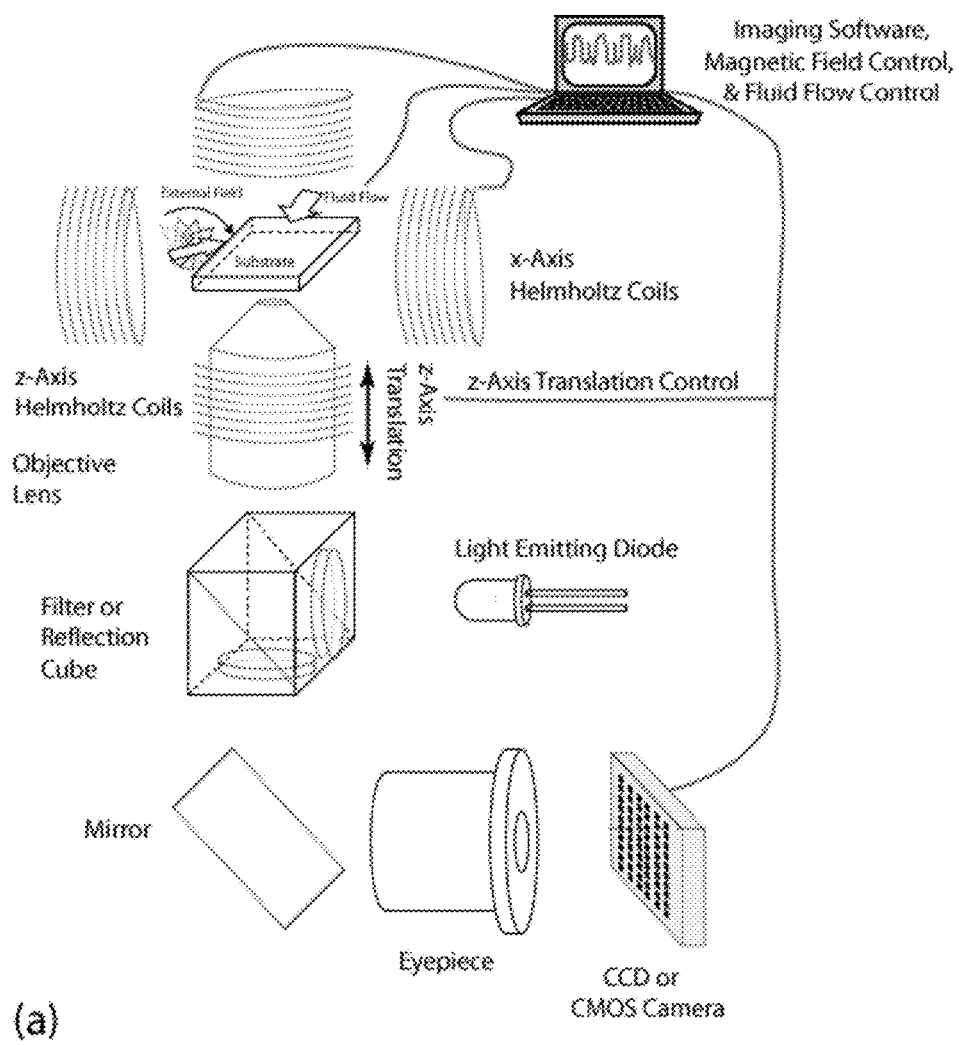
FIGS. 3a-c show exemplary devices of the present invention.
Figure 3:
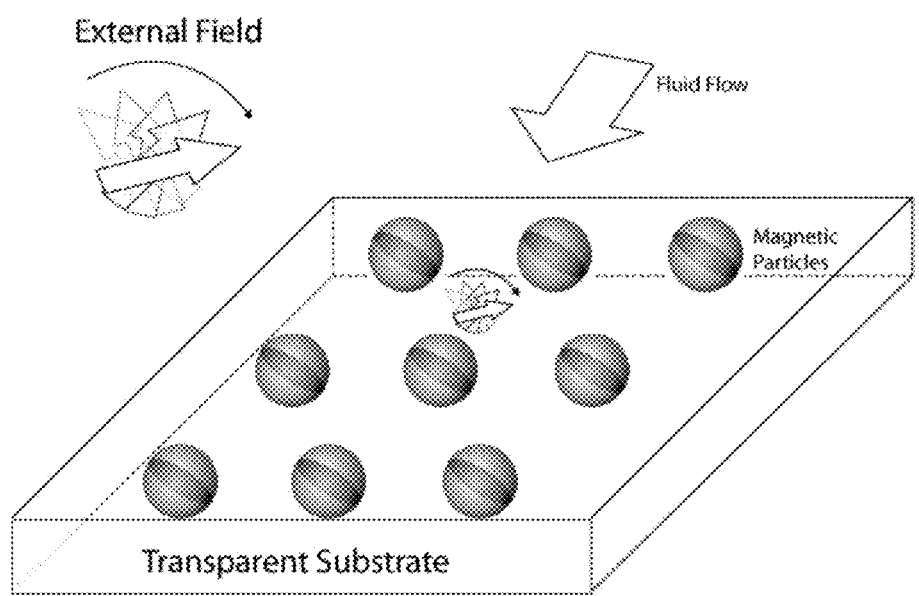
Figure 3:
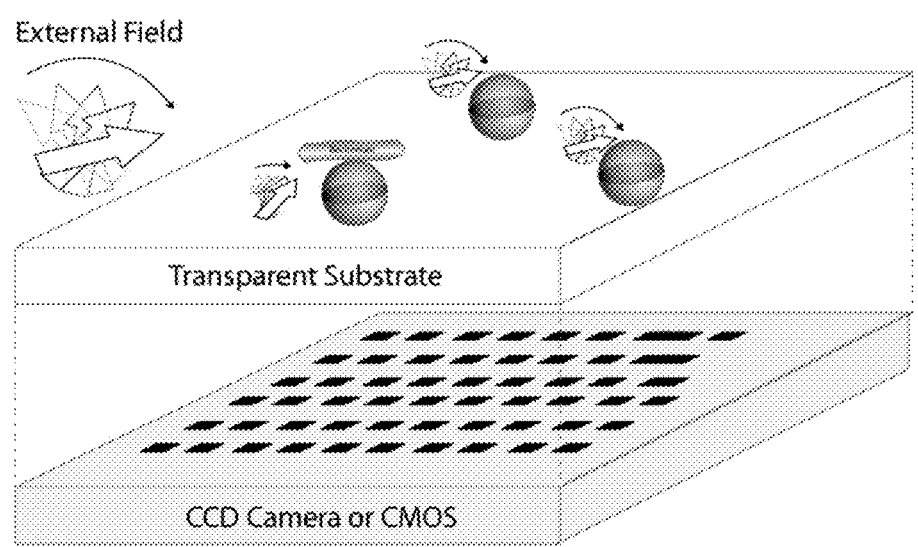

In some exemplary embodiments, the instrument, shown in FIG. 3(a), optically monitors the rotation of magnetic particles, allowing for measurement of single particle nonlinear rotation rates. Therefore, various applications can be carried out, including:

Detection of biological agents (e.g. bacteria, viruses, and biomolecules).
Characterization of bacterial growth, allowing for rapid antibiotic susceptibility measurements.
Measurement of viscosity.
Characterization of complex fluid and microrheological properties.

In some embodiments, the instrument holds spheres in place to prevent translation, but allows for rotational freedom. In an exemplary embodiment, the components of the instrument comprise, but are not limited to, one or more of:

1. A Set of Helmholtz Coils, which produces a rotating magnetic field in the x-z plane. In other embodiments, the Helmholtz coils are replaced by a permanent magnet that is rotated by an attached motor.
2. A Substrate that holds the fluid in place, providing an environment for the spheres to rotate in. The substrate, in some cases, also supports the spheres, as shown in FIG. 3(b).
3. A Fluidic Cell that holds the fluid in place, minimizing convection, and allows for fluid flow of analytes of interest, such as fluids containing biological agents, antibiotics, or viscous fluids.
4. Optics, which include an "objective lens" and an "eyepiece". The two components form a basic microscope, where the "mirror" allows for the optical path length to be completed under the instrument. Thus, a more compact instrument can be constructed.
5. A Light Emitting Diode (LED) illuminates the substrate with an excitation light source in the case of fluorescence, a means to reflect light off of the surface of the magnetic particles or for dark field microscopy.
6. A Filter Cube allows for the light of interest to pass to the camera. In the case of fluorescence, two filters are used (one for excitation filtering and one for emission filtering). In the case of reflection, the filter cube would only include a 50% transmission/50% reflection dichroic mirror.
7. A Camera that images the rotating particles, allowing for image analysis to be performed.
8. A Computer Interface that controls the magnetic field amplitude, magnetic field frequency, the position of the substrate ("z-axis translation control"), fluid flow, and image acquisition.
9. Software that performs data analysis of the acquired images.

While FIG. 3(a) shows magnetic particles being rotated in a plane perpendicular to the imaging plane, it is also possible to rotate magnetic particles in a plane parallel to the imaging plane. All applications can be carried out with particle rotation in either plane.

Non-magnetic micro and nanoparticles can also be rotated in this instrument with the replacement of magnetic fields with electric fields. These particles undergo the same rotational dynamics as magnetic particles. So, the rotating magnetic fields can be replaced with rotating electric fields to allow for identical applications. In such embodiments, particles are, for example, electrically polarized dielectrics or electrets.

An alternative construction of the instrument, shown in FIG. 3(a), includes the main components shown in FIG. 3(c). This approach eliminates the need for the "objective lens", "eyepiece" and "mirror" in FIG. 3(a). These components are eliminated by having the particles very close to a camera. This allows for direct measurement of any intensity variations that may result from a rotating particle. The position of the LED and the filtering is optimized for use embodiments.

As described above, in some embodiments, the devices of the present invention further comprise a fluorescence detection apparatus. Any suitable excitation source may be utilized including, but not limited to, a laser, an LED, a mercury lamp, or any other source that generates enough intensity light at the excitation wavelength. Illumination may occur at any angle with respect to the detector and magnetic field. In some embodiments where multiplex detection is desired, devices are designed to simultaneously detect particles fluorescing at different frequencies (e.g., to allow for the simultaneous detection of multiple types of microorganisms in the same sample). For example, in some embodiments, the device comprises a rotating filter wheel for detection of multiple wavelengths (See e.g., U.S. Pat. Nos. 5,171,534, 5,374,527; each of which is herein incorporated by reference). In other embodiments, multiple detectors are utilized (e.g., one detector per fluorescent dye). In still further embodiments, a diffraction grating is used to provide the entire spectrum of fluorescence from one line in the image. By moving the line across the image, a three-dimensional image with spectral intensity along the third axis is constructed.

In some embodiments, the device further comprises software or hardware for the demodulation of fluorescent signals. The fluorescent signal from the sample may have several frequency components. For example, it may have a steady background from autofluorescence, a signal at 1 Hz due to heart beats, a signal at 20 Hz due to muscle activity, a signal at 120 Hz due to stray room light flickering, and a signal from the indicator particles at the frequency of magnetic field rotation. The characteristic frequencies of the background noise are determined by measuring the fluorescent signal in time in the absence of any magnetic fields. The frequency of magnetic field rotation is then chosen to avoid any spikes in the background frequency spectrum (e.g., by measuring multiple frequencies). There are a number of methods to extract the signal that is at the frequency of the magnetic field rotation. For instance, in some embodiments, the Fourier transform of the intensity/time curve is taken, the size of the signal is at that frequency is utilized. In other embodiments, electronic filters or lock in amplifiers are utilized to select the desired frequency.

In some embodiments, demodulation is performed by taking two images: one with the particles oriented so that their fluorescence is "on," and the other with fluorescence "off." By subtracting the "off" images from the "on" images, constant background signals are removed leaving only an image of blinking (or moving) particles. In other embodiments, the spectrum from modulated particles is demodulated by taking two spectra, one with the particles oriented "on," and the other with the particles oriented "off." By subtracting the "off" spectrum from the "on" spectrum, constant background signals are removed leaving only the spectrum of the blinking, or moving particles.

In some embodiments, the background signal is utilized to provide information that is used in conjunction with information from magnetic probes. For example, autofluorescence from NADH may indicate metabolic activity. In other embodiments, fluorescence signal affected by blood pulses is measured by filtering signal intensities at the blood pulse rate.

Figure 6A:
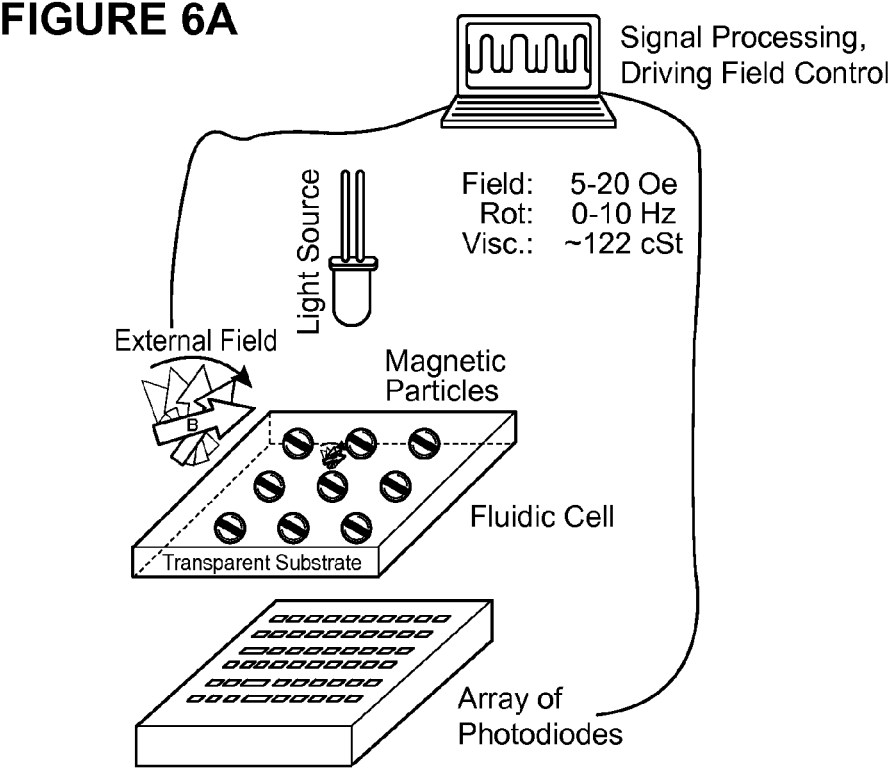
FIG. 6 shows exemplary devices of embodiments of the present invention. a) Schematic illustration of an exemplary device. b) Image of stand-alone-device that utilizes a 635 nm diode laser as a light source and photodiode to monitor single particle rotation.
Figure 6B:
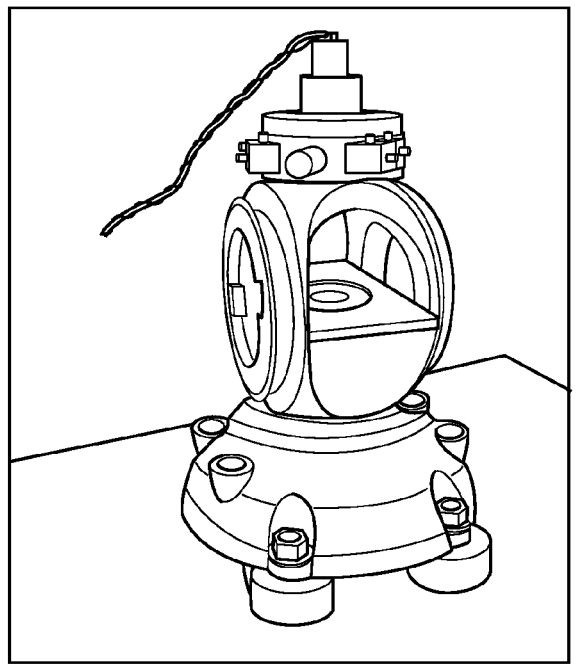

In other embodiments, devices such as those exemplified in FIG. 6 are utilized. Such devices utilize a detector or array of detectors (e.g., photodiodes) below a fluidic cell composed of a transparent substrate.

The device further comprises a light source. In some embodiments, the light source is a laser. In some embodiments, the laser in the device is focused so that the size of the beam is smaller than the particle. This allows for the entire beam to be blocked or passed, depending on the orientation of the particle being monitored, which maximizes the signal change. In other embodiments, the light source is a light emitting diode (LED), a xenon lamp, an incandescent light source, a gas discharge lamp, a fluorescent light source, or a diode-laser array. In some embodiments, the light source provides continuous illumination, pulsed source illumination, modulated illumination, white light illumination or filtered light illumination.

In some embodiments, devices utilize an array of magnetic microspheres in microwells, where only the light near or above the wells is passed through to the photodiodes (or camera). This allows for the light fluctuations caused by the particles to be observed without a focusing lens and thus maximizes the signal changes created by the rotating particles.

The devices of the present invention are not limited to a particular means of detection. In some embodiments, large nonlinear rotators (e.g., standard magnets, spheres, discs, rods, cubes, etc.) are utilized. In other embodiments, micro nonlinear rotators are utilized (e.g., magnetic nanoparticles, magnetic microspheres, magnetic granules, etc). In some embodiments, rotating electromagnetic fields, rotating electric fields, or other sources or electronically driven rotation are utilized.

Detection of binding of analytes and/or change in size of analytes can be monitored, for example, using amplification via labels (See e.g. above description of amplification by labels), linear to nonlinear rotation changes as described above, or magnetic separation in combination with nonlinear rotation rate changes.

In some embodiments, the device comprises rotators for rotating molecules of interest. Examples include, but are not limited to, magnetic rotators (e.g., permanent magnets, electromagnets or Helmholtz coils) or non magnetic rotators (e.g., for use in detecting rotation changes) (e.g., optical rotation or rotation with electric fields).

The present invention is not limited to a particular method of monitoring rotation of particles. Examples include, but are not limited to, passive method of monitoring rotation (e.g., hall sensors, magnetoresistance or impedance) and active method of monitoring rotation (e.g., transmission using a light source and photodiode or a CCD or CMOs camera, reflection, dark-field microscopy, polarized light detection, or fluorescence detection.

The present invention is not limited to the devices disclosed herein. One skilled in the art recognizes that substitutions or modifications of the disclosed devices may be utilized in the systems and methods of the present invention.

EXPERIMENTAL

The following examples serve to illustrate certain preferred embodiments and aspects of the present invention and are not to be construed as limiting the scope thereof.

Example 1

Detection of Bacteria

A 20 µL aliquot of 2.0 µm ferromagnetic microspheres functionalized with goat antimouse IgG (Spherotech IL) was spread onto a precut microscope slide and coated with 50 nm of Al. The sample was placed in a uniform magnetic field of 1.4 kOe so that the magnetization would be perpendicular to the microscope glass. The spheres were then rinsed with phosphate buffer solution (PBS) at a pH of 7.2 and suspended in 500 µL of PBS. The suspended sample was centrifuged at 9000 rpm for 8 minutes and re-suspended in 500 µL of PBS at a pH of 7.2. The sample was centrifuged once more at 9000 rpm for 8 minutes and the supernatant was removed. 100 µL of mouse anti-*E. coli* IgG (Cortex Biochem, San Diego, Calif.) was added to the pellet of magnetic microspheres. The primary antibody and the magnetic microspheres were allowed to incubate at room temperature for 4 hours. The excess primary antibody was removed by centrifuging the sample at 9000 rpm for 8 minutes and the supernatant was discarded. Finally, the magnetic microspheres were re-suspended into 500 µL of PBS. At each of the above stages the sample was vortexed at 3000 rpm for 15 seconds.

To make the bacteria fluorescent, a DsRed plasmid was used with *Escherichia coli* BL21(DE3) following previously described transformation procedures. The bacteria were allowed to reproduce until the sample had an optical density of 0.67 at 600 nm and was stored at 4° C. The magnetic microspheres functionalized with anti-*E. coli* antibody and mixed 1:1 with the now fluorescent *E. coli*. To aid in binding, the sample was centrifuged at 9000 rpm for 8 minutes. The sample was then vortexed at 3000 rpm for 15 seconds and allowed to incubate. The resulting sample had many single microspheres with 1-5 *E. coli* bound to their surface, where visual analysis was used to confirm the presence of a single bacterium.

Two homemade ~100 μm thick fluidic cells were fabricated: one fluidic cell contained the magnetic microsphere solution before bacteria were added and the other had magnetic microspheres with bacteria bound to their surfaces. Before being placed in the fluidic cells, the samples were mixed with glycerol so that the glycerol-water mass fraction was 0.5. The nonlinear rotation frequencies for 20 single magnetic microspheres, without bacteria, were obtained by monitoring the intensity fluctuations caused by light reflecting off of the aluminum half-shell. From the other fluidic cell, 20 nonlinear rotation frequencies were obtained for single magnetic microspheres with one *E. coli* bound to their surfaces by monitoring the intensity fluctuations caused by the bacteria fluorescence. The average rotation frequencies were determined by taking a fast Fourier transform of the microspheres' intensity fluctuations—see FIG. 2(*b*). The rotational frequencies were then averaged and compared to determine the rotation frequency changes caused by the bacteria.

Figure 2:
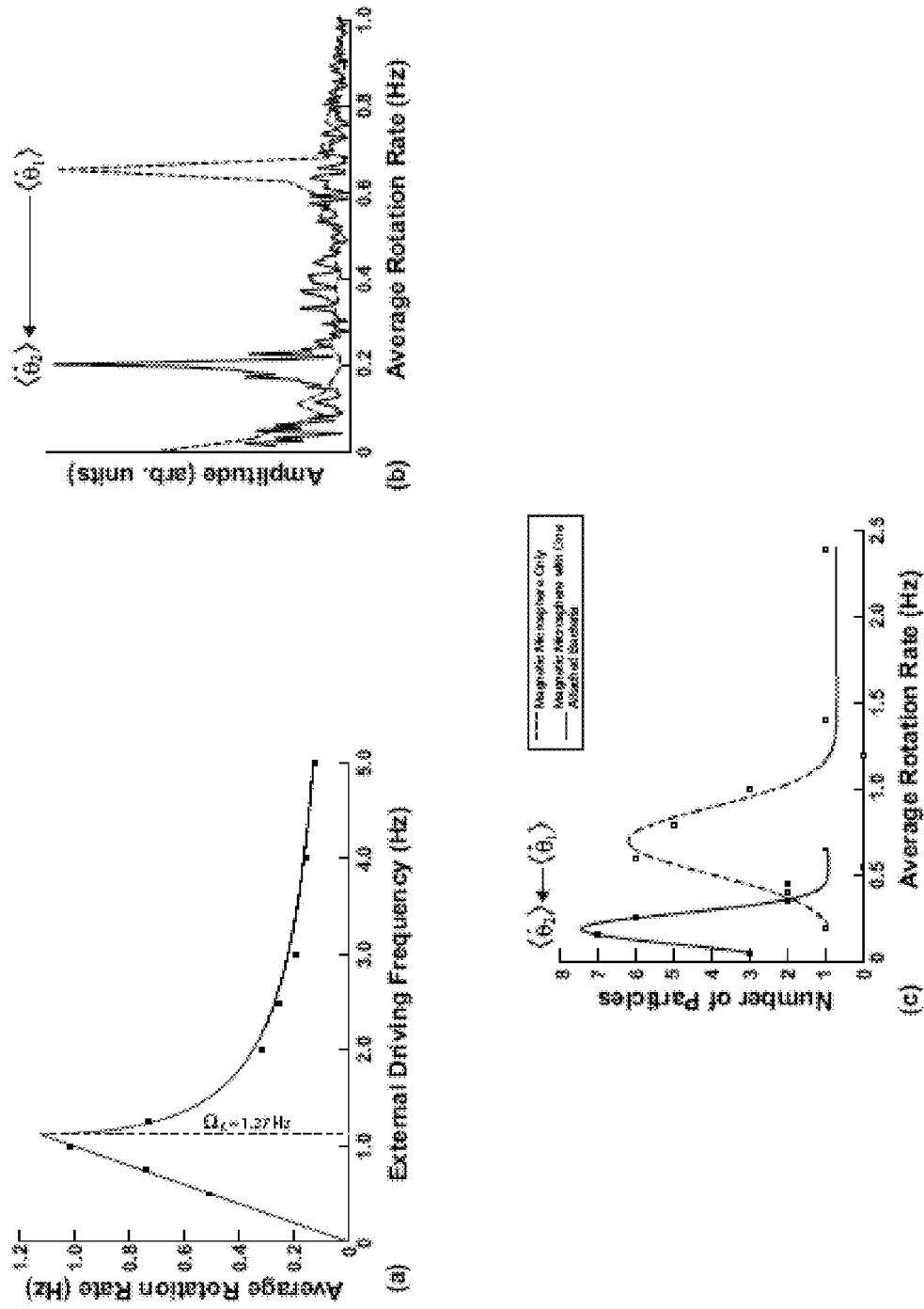
FIG. 2. a) The rotational response of a single magnetic particle with attached bacteria at various external driving frequencies, where the squares are data and the line is a theoretical fit. b) The fast Fourier transform of the intensity fluctuations of a typical particle with bacteria attached (solid curve) and for one without (dashed curve). c) The average nonlinear rotation frequency of 20 particles in a fluidic cell with bacteria present (solid curve) and a fluidic cell without bacteria (dashed curve). The magnetic microspheres with one bacterium attached rotated 33.8 times slower then the blank micro-stages (particles).

The theory for a single magnetic particle rotating in response to an external driving field has been described (McNaughton et al., Journal of Physical Chemistry B 110, 18958 (2006); McNaughton et al., Sensors and Actuators B 121, 330 (2007); Cebers and M. Ozols, Physical Review E 73, 21505 (2006), each of which is herein incorporated by reference in its entirety; Examples 2 and 3 below). FIG. 2(*a*) shows the average rotation frequency of such a system for increasing external driving frequencies. The data is in good agreement with the fit determined from Equation 2 and the critical slipping frequency, $\Omega_c$, was found to be 1.27 Hz. Since the rotational dynamics of the magnetic particle were in good agreement with Equation 2, any forces resulting from bacterial motility are negligible. This measurement shows that when a bacterium is bound to the surface of a magnetic microsphere, the system can still be analyzed using previously developed theory (McNaughton et al., 2006, supra; McNaughton et al., 2007, supra). Thus, a change in rotation rate can then be used to detect bacteria.

While the entire range of frequencies for magnetic particles with and without bacteria could be scanned as was done in FIG. 2(*a*), it is much faster and more straightforward to only measure the value of the nonlinear rotation frequency, $\langle \dot\theta \rangle$, at a given external driving frequency of $\Omega$. FIG. 2(*b*) shows this measurement for a typical magnetic microsphere with a single bacterium attached to its surface and for one without. FIG. 2(*c*) shows the curves for the rotation frequency of 20 particles in a fluidic cell with bacteria and for 20 particles in one without bacteria. The presence of the bacteria on the surface of the magnetic microspheres caused a measurable change in the average rotation frequency, namely the average frequency of the particles at a driving frequency of 4.0 Hz changed from $\langle \dot\theta \rangle$=0.72 Hz to $\langle \dot\theta \rangle$=0.19 Hz, a factor of ~3.8. Once a bacterium is attached to a magnetic microsphere, this technique can also be used to monitor single bacteria growth, which finds use in the study of single bacteria growth dynamics and for rapid antibiotic susceptibility measurements.

The ability to use the change in nonlinear rotation of magnetic particles to detect bacteria has been demonstrated. The nonlinear rotation frequency of 2.0 μm magnetic microspheres changed on average from 0.72 Hz without a bacterium to 0.19 Hz with a single bacterium attached, where the driving oscillatory magnetic field was at a frequency of 4.0 Hz.

Example 2

Non-Linear Rotation

A. Theory

Equation of Motion for Magnetically Driven Rotor with Drag

The equation of motion for a magnetic particle, in a viscous solution, torqued by an external magnetic field, B, is given by (Valberg et al., Biophys. J. 1987, 52, 537)

$$I\frac{d^2\theta}{dt^2} - \gamma\frac{d\theta}{dt} = mB\sin(\phi), \quad (1)$$

where I is the moment of inertia, t is time, γ is the drag coefficient, θ is the angular orientation of the magnetic moment, m is the total magnetic moment of the particle, and φ is the phase lag, which is the angle between the external magnetic field and the magnetic moment. For the simple case of an external magnetic field rotating continuously in a circle, the magnetic torque is given by $\Gamma_m$=m×B=mB sin(φ)=mB sin(Ωt−θ), where Ω is the rotation rate of the external field. For low Reynolds numbers the inertial term may be neglected (Purcell et al., American Journal of Physics 1977, 45, 3). Thus, rewriting Equation 1 in a nondimensional form, after neglecting inertia, reduces the equation of motion to the nonuniform oscillator equation, $$\frac{d\phi}{d\tau} = \frac{\Omega}{\Omega_c} - \sin(\phi), \quad (2)$$

where $$\Omega_c = \frac{mB}{\gamma}, \tau = \Omega_c t,$$

and φ=Ωt−θ. Analogous "non uniform oscillator" equations have successfully described a variety of systems, including optical rotation of glass nanorods[9], the flashing of fireflies[29], and the voltage oscillations in Josephson junctions (Strogatz, Nonlinear dynamics and chaos; Westview Press: Cambridge, Mass., 2000).

The Non Uniform Oscillator

Equation 2 is formally known as the nonuniform oscillator equation (Strogatz, supra) and has two solutions that indicate two different types of rotational behavior. If the external magnetic field frequency is below a critical rotation rate, $\Omega_c$, then the magnetic particle will rotate at the same rate as the external field with a phase lag that increases with the external rotation rate, $\phi=\sin^{-1}(\gamma\Omega/mB)$. The maximum rotation rate occurs when φ=π/2 and Ω=$\Omega_c$. However, if the external magnetic field frequency is higher than $\Omega_c$, the magnetic particle experiences a fast rocking motion superimposed on a slower net rotation rate which decreases with increasing external driving rate, exhibiting a nonlinear relationship. The magnetic particle is acting as a nonuniform oscillator with a phase lag that "critically slips" at $\Omega_c$ and can be described, for the simple case of γ=κηV, giving $$\Omega_c = \frac{mB}{\gamma} = \frac{mB}{\kappa \eta V}, \quad (3)$$

where κ is the shape factor, which for a sphere is 6, η is the dynamic viscosity, and V is the particle volume. This considers the simple case of a field rotating a particle, in two dimensions, with a resultant constant drag. More complicated critical phase-slipping behavior can result from a variety of scenarios, such as using external magnetic fields strong enough to affect the magnetic moment of the particles or by having nonuniformities in the external magnetic field. Similar cases of critical phase-slipping behavior has also been observed in optically torqued glass nanorods (Shelton et al., Phys. Rev. E 2005, 71, 036204), paramagnetic chains used as micromixers (Biswal et al., Anal. Chem. 2004, 76, 6448), carbon nanotubes loaded with magnetic nanoparticles (Korneva et al., Nano Lett. 2005, 5, 879) and MagMOONs (Behrend et al., Magn. Magn. Mater. 2005, 293, 663). The above parameters in Equation 3 can be exploited for a variety of applications—see Table 1. For instance, with a given particle and a given field, Equation 3 will give the change in viscosity that occurs due to a change in temperature, or due to a biological change. Also, by measuring the values of the "Constants" in Table 1, it is possible to calculate the "Determinable Values" shown in Table 1.

TABLE 1

The various physical parameters that can be determined, using Equation 3, if a value for the critical slipping rate, $\Omega_c$, is experimentally measured. Also shown are the applications of determining these parameters.
Applications of Measuring the Critical Slipping Rate, $\Omega_c = mB/\kappa \eta V$

| Constant | Determinable Value | Applications |
|---|---|---|
| B, κ, η and V | m: Magnetic Moment | Measurement of moment, magnetic content, and particle uniformity of synthesized particles. |
| m, κ, η and V | B: Magnetic Field | Measurement of local rotating magnetic fields. |
| m, B, κ and V | η: Viscosity | Measurement of effective viscosity near an interface, local viscosity and spatial viscosity. |
| m, B, and η | κV: Shape Factor and Volume | Detection of single particle binding events that will result from shape and volume changes. |

From Linear to Nonlinear: Behavior of Driven and Dragged Rotation

The linear to nonlinear behavior, characteristic below and above the critical slipping rate, can be symbolically described by calculating the average rotation rate of the rotating particle, and is given by $$\left\langle \frac{d\theta}{dt} \right\rangle = \begin{cases} \Omega, & \Omega < \Omega_c \\ \Omega - \sqrt{\Omega^2 - \Omega_c^2}, & \Omega > \Omega_c \end{cases}. \quad (4)$$

Experimentally, $\langle d\theta/dt \rangle$ can be determined from tracking the particle orientation in time and by taking a fast Fourier transform (see Analysis in Experimental Section below). A value for $\Omega_c$ can then be determined by performing a least squares fit on $\langle d\theta/dt \rangle$ versus $\Omega$ (see Results and Discussion below).

As can be seen from Equation 3 and Table 1, measurements of $\Omega_c$ allows for the determination of a variety of physical values. Alternatively, if one of the parameters such as viscosity is altered, then the critical slipping rate, $\Omega_c$, will also change. This would be the case for varying the temperature in a glycerol environment (Shankar et al., Proc. R. Soc. Lond. A 1994, 444, 573) and therefore, the probe could be used as a temperature/viscosity probe. Another parameter that can be manipulated is the particle volume. This can be done by modifying the surface chemistry of the particle so that selectable biological antigens will attach to its surface. For instance, when an antigen is attached, the effective hydrodynamic volume of the magnetic particle will be changed, causing a change in the critical slipping rate. By combining this type of critical phase-slipping behavior with chemical sensing, chemical concentrations can be measured while physical changes are monitored, giving a multi-sensing platform.

B. Experimental

Preparation of Sol Gel Particles with SNARF-1 and Barium Ferrite

Following a modification of the Stöber Method (Stober et al., Journal of Colloid and Interface Science 1968, 26, 62) developed by Nozawa et al. (Langmuir 2005, 21, 1516), approximately 25 mg of 40-60 nm barium ferrite nanopowder (Sigma-Aldrich) was sonicated for several minutes in 12.5 ml of ethanol (Sigma-Aldrich), resulting in a weight percent solids of 0.2%. To this, 2.38 mL of ammonium hydroxide (Sigma-Aldrich) and 400 µL of 5mg/mL SNARF-dextran (Invitrogen/Molecular Probes) were added. This solution was placed in a three-necked round-bottomed flask and purged with argon. A condenser was placed in one of the necks of the round-bottomed flask to keep the reactants from evaporating, and the other two necks were sealed with rubber stoppers. Then, a solution of 7.5 mL of ethanol and 1.25 mL tetraethyl orthosilicate (TEOS) (Sigma-Aldrich) was placed in a 10 mL syringe. PEEK tubing, with an interior diameter of 0.13 mm was attached to the end of the syringe and inserted into a rubber-capped neck of the round-bottomed flask so that the end of the tubing was just above the solution level. The syringe was placed in a syringe pump, and the contents were added to the round-bottomed flask at a flow rate of ~0.5 mL/hr. Throughout the addition, the solution in the round-bottomed flask was stirred at a constant rate of 500 rpm and temperature of 20.5° C. After the complete addition of the solution in the syringe, the reaction was allowed to stir for 12 hours. The particles were then rinsed with ethanol via centrifugation using a speed of 5000 rpm for 15 minutes, and they were collected by filtering through a 0.2 µm Whatman Anodisc filter membrane with ethanol.

Viscous pH Buffer Preparation and Suspension pH buffers (50 mM Phosphate) of pH 6.6 and pH 8.8 were prepared and mixed 1:1 by mass with 99.5+% glycerol (Sigma-Aldrich). This produced a 0.5 glycerol mass fraction, which has a reported kinematic viscosity at 20° C. of 5.26 centistokes[30] (for comparison, the viscosity of pure water at 20° C. is 1.01 centistokes). The particles were then suspended in the viscous pH buffers, yielding a concentration of approximately $1 \times 10^8$ particles per mL, where they were magnetized and then sonicated for several minutes. Changes in pH, measured with a pH meter, were within 0.1 pH units after the addition of glycerol and the particles. However, it is contemplated that any observed minor changes were related to loose barium ferrite particles that were not encapsulated in the silica matrix during synthesis. An alternative method takes advantage of a new method[22] that uses cobalt or iron coated with silver or gold, which avoids such chemical effects and, therefore, any changes in pH. Finally, each solution was pipetted into two different homemade fluidic cells, with a typical chamber thickness of ~100 pm, width of ~6.5 mm, and length of ~22 mm.

Microscopy

All microscopic images were obtained with a Roper Coolsnap ES CCD camera (Roper Scientific Tucson, Az) connected with an Olympus IMT-II (Lake Success, N.Y.) inverted epifluorescence microscope, see FIG. 2. A Lambda DG-4 Xenon Lamp (Sutter Instruments, Novato, Calif.) and an Olympus blue filter cube were used for fluorescence studies. The objective lens used to obtain bright field images, fluorescent images, and fluorescence spectroscopy was an Edmund Optics 60× magnification lens with a numerical aperture of 0.85. Spectroscopic data was obtained with an Acton Research Corp spectrometer connected to a Hamamatsu 230 CCD. The camera frame rate for experiments performed under bright field microscopy was ~32 frames per second, while fluorescence images were obtained in a single image acquisition mode. In order to observe a significant signal for acquisition of fluorescence spectra, it is preferred that a minimum of three 1-10 μm particles should be in the microscope's field of view, which was approximately equivalent to weight percent solids of 0.1% of sensing particles to water.

Magnetic Particle Rotation

Particles were observed in the aforementioned ~100 pm thick fluidic cell near a glass-water interface, at a distance of a micron or less. Rotation was carried out with a digital function generator that was used to rotate a stepper motor connected to a ⅝" diameter, diametrically magnetized Alnico magnet (Dexter Magnetics, Inc.). The magnet was placed in a vertical orientation ~12 cm to the side of the sample so that the magnetic field was rotated in the focal plane with a magnitude of ~6 Oe and at speeds ranging from 0 to 2.5 rotations per second. The particle was observed to be actively rotated by this external rotation field and since no translation was observed, any magnetic gradient forces produced by the external field were negligible. Also, no significant gradient is expected over the microdomain of one particle. Generally, the pH sensing magnetic particle aligned with the field along its geometric easy axis of magnetization (along its length). The glass interface confined the motion to 2-dimensions, reducing tumbling and simplifying the analysis.

Analysis

Images were acquired and analyzed using Metamorph software (Universal Imaging Corp, Sunnyvale, Calif.) with bright field microscopy. The Metamorph particle tracking function was used to track in time the vertical displacement of the corner of a magnetic particle. For each rotation the corner of the particle will be furthest away at half a rotation and return back to the origin after one full rotation, see "In-Plane Rotation". In this way, the vertical displacement roughly expresses the sine of the angle and made it possible to monitor the orientation of the particle. Then, a fast Fourier transform was applied to the time series to obtain the average rotation rate.

This type of image analysis was only possible because of the shape asymmetry of the observed particle. Shape asymmetries similar to that of the particle used to obtain the data discussed in the results section was typical in batches of synthesized particles.

C. Results and Discussion

Fluorescence Characterization of Micro-Particles

To ensure that the pH sensing magnetic particle contained fluorescent dye, the fluorescent images of the particles were checked. The shape of the particle imaged with fluorescence microscopy is similar to the shape of the same particle under bright field microscopy, indicating that fluorescent dye was concentrated within the particle. The sizes of the particles used in these experiments were on the order of 1-10 microns. The large particle size and irregular shapes may have resulted from aggregation of the barium ferrite nanoparticles during synthesis. However, 5 μm particles were attached to human bronchial epithelial cells and used to study the microrheology (Puig-de-Morales et al., J Appl Physiol 2001, 91, 1152) of the cells.

After checking the fluorescent images of the particles, the fluorescence emission spectra of the particles in pH 6.6 and pH 8.8 glycerol buffer solutions were obtained. The resulting spectra demonstrate that the particles were sensitive to a change of pH from 6.6 to 8.8. The location of the emission maximum changed from a short wavelength acidic peak, at ~585 nm, to a longer wavelength basic peak, at ~637 nm. This change in peak location is expected for SNARF-1 (Haugland, R. P. The Handbook—A Guide to Fluorescent Probes and Labeling Technologies Tenth ed.; Invitrogen, 2005). While there was a small amount of photobleaching, it did not occur at a rate that affected measurements.

Sudden Breakdown of Linear Response: Critical Phase-Slipping

Having obtained pH dependant spectra, bright field microscopy was used to monitor the magnetic particle. Particles were monitored at at different times and orientations before critical phase-slipping, top row, and after critical phase-slipping, bottom rows. At an external field rotation rate of $\pi/2$ rad/s (0.25 rotations/s), the particle rotates in phase with the external magnetic field. At each time step, the particle progresses in the same clockwise direction—never rotating in a direction opposite to the driving field. However, when the external field rotation rate is increased from $\pi/2$ rad/s to $4\pi$ rad/s (2.0 rotations/s, i.e. above the critical slipping rate), the particle generally rotates in the clockwise direction but occasionally rocks in the opposite direction. It is a result of the viscous drag becoming too high, in comparison with the magnetic torque. This is the type of rotational behavior that causes the particle to have a lower average rotation rate than that of the external field Tracking a corner of the particle and plotting the vertical displacement it travels from its origin allows for measurement of the particle's average rotation rate. Before critical phase-slipping, the vertical displacement appears to be sinusoidal in time and the average rotation rate of the magnetic particle was found by taking a Fourier transform. Above the critical slipping rate, the periodic behavior of the particle reveals a high frequency oscillation, due to the regular rocking being superimposed on the slower frequency oscillation that results from the gradual clockwise progression of the particle. The magnetic particle is being lapped by the external field and to minimize torque, the particle momentarily "rocks" in a direction opposite to that of the external field. Thus, the particle is rocking once per rotation of the external field. These two oscillations are seen in the Fourier transform, where the largest peak is the slower average rotation rate, ~0.31 Hz, and the smaller peak is the faster rotation rate, ~2.0 Hz, of the external field, seen through the intermittent counter-clockwise rotations of the particle.

The average rotation rate of the magnetic particle, at various external field rotation rates, was determined from the data. The change of behavior due to phase-slipping can be seen as the external field rotation rate is increased. Initially, the relationship is linear, with a one-to-one correspondence, so that when the external rotation rate is doubled the average particle rotation rate is also doubled. However, at driving frequencies above the critical slipping rate, the rotational behavior is nonlinear and the average rotation rate of the particle gets slower for increasing external field rotation rates. The slower rotation rate is due to the frequent rocking (also referred to as "flip backs" (Shelton et al., Phys. Rev. E 2005, 71, 036204) or "swaying" (Biswal et al., Anal. Chem. 2004, 76, 6448). Fitting Equation 4 to the experimental data points, using a least squares fit, gives a critical slipping rate of ~6.8 rad/s (1.1 rotations/s).

The data deviates slightly from the theoretical fit. Most notably, the particle's average speed goes down faster than what would be expected with the theory of a particle in free solution. However, the critical slipping rate was reproducible. The critical slipping rate was estimated by slowly varying the rotation rate, from above and below the critical slipping rate, and watching for any rotations opposing the direction of the external field to occur. Using this technique, the critical phase-slipping was reproducibly found to be in the range of ~6.75 rad/s to ~7.2 rad/s, which agrees with the critical slipping rate of ~6.8 rad/s that was determined from fitting the data.

Being able to determine the critical slipping rate is useful because it is sensitive to physical properties such as viscosity, the particle's magnetic moment, external magnetic fields, and size, see Table 1. In order to obtain absolute measurements for any of these parameters, the other parameters should be known. If the same particle is monitored while parameters of the system are altered, then measurements with only a single particle are uniform.

Example 3

Physiochemical Microparticle Sensors Based on Nonlinear Magnetic Oscillations

A. Theoretical Review
2.1. Equation of Motion

While there are well-developed theories on rotating magnetic systems(Cēbers et al., Phys. Rev. E 73 (2006) 021505, McNaughton et al., Newman et al., Journal of Applied Physics 39 (1968) 5566, Valberg et al., Biophys. J. 52 (1987) 537-550, Gitterman et al., Eur. J. Phys. 23 (2002) 119-122)] few application-oriented theories or experiments for single particle systems that exhibit nonlinear rotations have been published. Cēbers and Ozols have performed a rigorous theoretical analysis on single particle systems, but did not focus on applications except to describe rotation of magnetobacteria and to suggest mass transfer applications (Cēbers et al., supra). In this section, the theory for a single magnetic particle is reviewed and applications are discussed.

The magnetic torque that acts on a magnetic probe, which is given by $$|\Gamma_{mag}| = |m \times B| \quad (1)$$
$$= mB\sin(\Omega t - \theta),$$

where m is the magnetic moment, B is the external magnetic field, and $\Omega t - \theta$ is the angle between the external field and the magnetic moment. If the external magnetic field is much smaller than that required to remagnetize the magnetic probe while the torque is larger than the Brownian torques, then the equation of motion is given by (Valberg et al., supra)

$$I\ddot{\theta} - \gamma\dot{\theta} + mB\sin(\Omega t - \theta) = 0 \quad (2)$$

where I is the moment of inertia and γ is the drag coefficient. To simplify the number of parameters, Equation 2 can be made dimensionless by allowing $$\Omega_c = \frac{mB}{\gamma}, \tau = \Omega_c t, \text{ and } \phi = \Omega t - \theta. \quad (3)$$

Given these expressions, Equation 2 can be expressed as $$\frac{I\Omega_c}{\gamma}\frac{d^2\phi}{d\tau^2} + \frac{d\phi}{d\tau} = \frac{\Omega}{\Omega_c} - \sin(\phi). \quad (4)$$

2.2. Reynolds Number

For most magnetic micro- and nanoparticles, the inertial term in Equation 4 is negligible. This can be determined from the Reynolds number, a dimensionless quantity equal to the ratio of the inertial force to the drag force; for a rotating sphere the Reynolds number is $$Re = \frac{r^2\rho\dot{\theta}}{\eta} = \frac{r^2\dot{\theta}}{\nu}, \quad (5)$$

where r is the radius of a sphere, ρ is the density of the fluid, $\dot{\theta}$ is the rotation rate of the sphere, η is the dynamic viscosity, and ν is the kinematic viscosity. A low Reynolds number is equivalent to the condition $(I\Omega_c/\gamma) \ll 1$ from Equation 4. For example, a typical 5.0 μm magnetic microsphere in pure glycerol at 20° C., which has a reported kinematic viscosity of 1160 cSt (Shankar et al., Proc. R. Soc. Lond. A 444 (1994) 573-581), rotating at ~63 rad/s (10 rotations/s) will have a Reynolds number of ~3.4×10$^{-7}$. Thus, the condition that allows inertia to be neglected, Re<<1, is satisfied. In all low Reynolds number environments, such inertial effects are negligible (Purcell et al., American Journal of Physics 45 (1977) 3-11). When smaller spheres are used, Re becomes even less significant. The experiments performed herein had negligible inertia due to low Reynolds numbers.

2.3. Nonuniform Oscillator Equation

From Section 2.2, it is clear that the system under investigation is in a low Reynolds number regime and inertia can be ignored. Ignoring inertia allows Equation 4 to be rewritten in the form of the nonuniform oscillator equation, $$\frac{d\phi}{d\tau} = \frac{\Omega}{\Omega_c} - \sin(\phi), \quad (6)$$

which also describes voltages across a Josephson Junction (Strogatz, Nonlinear dynamics and chaos, Westview Press, Cambridge, Mass., 2000) the optical torquing of a glass nanorod (Shelton et al., Phys. Rev. E 71 (2005) 036204), and even the flashing of a firefly (Strogatz, supra). The measurable quantity of optically anisotropic particles is the intensity modulation produced as they rotate. This intensity depends on the particle's orientation angle, which can be calculated, but it is more straightforward to measure the average rotation rate from the particle's intensity. Given Equation 6, the period of rotation and, therefore, the average rotation rate can be determined. The period is given by $$T = \int dt = \frac{1}{\Omega_c} \int \frac{d\tau}{d\phi} d\phi \qquad (7)$$

$$= \int_0^{2\pi} \frac{d\phi}{\Omega - \Omega_c \sin(\phi)}$$

$$= \frac{2\pi}{\sqrt{\Omega^2 - \Omega_c^2}}.$$

Therefore, the average rotation rate, $\langle d\theta/dt \rangle$, can be solved for rates both higher and lower than the critical slipping rate. These two solutions are given by $$\left\langle \frac{d\theta}{dt} \right\rangle = \begin{cases} \Omega & \Omega < \Omega_c \\ \Omega - \sqrt{\Omega^2 - \Omega_c^2} & \Omega > \Omega_c \end{cases}. \qquad (8)$$

If inertia is kept in Equation 4, then numerical integration methods such as the Runge-Kutta method can be used to approximate $\langle d\theta/dt \rangle$. When inertia is considered, then $\Omega_c$ will depend on the direction from which the critical value is approached (Strogatz, supra). This arises from the inertia of the particle undergoing rotation, which would oppose the particle's tendency to realign with the external field. While this numerical solution has not been performed for spherical probes, it has been numerically solved and experimented with in order to determine the critical slipping of a magnetic microdrill (a cylindrical magnet with a spiral blade wrapped around its body, which is on the order of a millimeter in diameter) (Yamazaki et al., Sensors and Actuators A 105 (2003) 103-108, Ishiyama et al., IEEE Trans. Magn. 37 (2001)].

The conditions and environments where the analysis is valid can be further clarified by defining a Reynolds number based on the maximum rotation rate of a rotating particle. This maximum rotation is given by $\Omega_c$; therefore, Equation 5 can be rewritten as $$Re_{max} = \frac{r^2 \dot\theta_{max}}{\nu} = \frac{r^2 \Omega_c}{\nu} = \frac{mBr^2}{\kappa V \rho \nu^2}, \qquad (9)$$

where $\kappa$ is the shape factor, $\rho$ is the density of the fluid, and $V$ is the volume of the particle. For a sphere, this becomes $$Re_{max} = \frac{mB}{8\pi r \rho \nu^2}. \qquad (10)$$

The value calculated from Equation 10 is significant because it gives the highest value that the Reynolds number can have in a given system. Therefore, it is a good indicator of whether or not inertia can be ignored at all rotation rates.

2.4. Rotation of Ellipsoidal Shapes

The critical slipping rate can be determined for a variety of shapes, sizes and conditions. For example, an ellipsoid will have a different critical slipping rate than that of a similarly sized sphere due to the change in the shape factor. For a particle rotating in a low Reynolds number environment, this point of criticality is given by $$\Omega_c = \frac{mB}{\kappa \eta V}, \qquad (11)$$

where, for an ellipsoid with major axis a and minor axis b, $\kappa$ can be determined from the equation (Valberg et al., supra)

$$\kappa = \frac{1.6[3(a/b)^2 + 2]}{1 + \zeta - 0.5\zeta(b/a)^2}, \quad \text{where} \qquad (12)$$

$$\zeta = \frac{1}{\varepsilon^3}\left[\ln\left(\frac{1+\varepsilon}{1-\varepsilon}\right) - 2\varepsilon\right] \text{ and} \qquad (13)$$

$$\varepsilon = \sqrt{1 - (b/a)^2} \quad (a \geq b). \qquad (14)$$

For a sphere, a=b and the shape factor becomes 6. Another example is a chain of N spheres, and for N≥3 the shape factor is given by (Biswal et al., Anal. Chem. 76 (2004) 6448-6455)

$$\kappa = \frac{2N^2}{\ln(N/2)} \qquad (15)$$

This would result in a modified critical slipping rate of $$\Omega_c = \frac{\ln(N/2)mB}{2N^2 \eta V} \qquad (16)$$

2.5. Real-Time Measurements by Nonlinear Rotation

The entire rotational behavior of single particles can be measured to determine the value of the critical slipping rate. This technique involves measuring the rotation response of a magnetic microsphere at varying external driving frequencies (see Section 3.4). It is also possible to determine the critical slipping rate by measuring the rotation rate of the particle at a single external rotation rate that is greater than the critical slipping rate, e.g. when $\Omega > \Omega_c$. Recall that the equation for the nonlinear rotational regime is $$\left\langle \frac{d\theta}{dt} \right\rangle = \Omega - \sqrt{\Omega^2 - \Omega_c^2} \quad \Omega > \Omega_c. \qquad (17)$$

By solving Equation 17 for the critical slipping rate:

$$\Omega_c = \langle \dot\theta \rangle^{\frac{1}{2}} [2\Omega - \langle \dot\theta \rangle]^{\frac{1}{2}} = \frac{mB}{\kappa \eta V}. \qquad (18)$$

With Equation 18, one can determine physical values by measuring one average nonlinear rotation rate, namely by solving for m, B, $\kappa$, $\eta$, or V. This makes measuring physical changes, such as viscosity or volume changes, especially straightforward and fast. This is the technique used to measure the viscosity changes in section 4.3 as well as the binding and dissociation events in the experiments in Section 4.4 below.

2.6. Example of Real-Time Measurements: Viscosity

By using Equation 18 a variety of parameters can be measured, the example of viscosity is given herein. When monitoring a nonlinear rotating sphere in a fluid, the average rotation rate, $\langle \dot\theta \rangle$, will change when the viscosity is changed. One way to change the viscosity of a fluid is to alter its temperature. The temperature dependence of glycerol-water mixtures has been accurately characterized and is given by $v=v(T)=\exp(a+bT+cT^2)$ (P. N. Shankar, M. Kumar, Experimental Determination of the Kinematic Viscosity of Glycerol-Water Mixtures, Proc. R. Soc. Lond. A 444 (1994) 573-581) and the critical slipping rate can therefore be rewritten as $$\Omega_c(v(T)) = \frac{mB}{\rho \kappa V} \frac{1}{\exp(a+bT+cT^2)}, \quad (19)$$

where a, b, and c are material-dependant constants (Shankar et al., Proc. R. Soc. Lond. A 444 (1994) 573-58 1). If $\Omega_c$ is measured in a fluid with a known viscosity at $T_1$, the temperature is changed to $T_2$, and $\Omega_c$ is measured again, then the viscosity of the fluid at $T_2$ can be calculated, namely $$v(T_2) = \frac{v(T_1)\Omega_c(T_1)}{\Omega_c(T_2)} = v(T_1)\left[\frac{\langle\dot\theta\rangle_{T_1}}{\langle\dot\theta\rangle_{T_2}}\right]^{\frac{1}{2}}\left[\frac{2\Omega - \langle\dot\theta\rangle_{T_1}}{2\Omega - \langle\dot\theta\rangle_{T_2}}\right]^{\frac{1}{2}} \quad (20)$$

This is the technique that is used in section 4.3 to measure viscosity and is especially useful when the exact value of the particle volume or magnetic moment is unknown.

3. Experimental 3.1. Preparation of Magnetic Particles 3.1.1. Preparation of Fluorescent Half-Shell Particles Fluorescent magnetic microspheres with a diameter of 4.6 µm, obtained from Spherotech, Inc. (Libertyville, Ill.), were dispersed into a monolayer supported by a glass substrate. This slide was then placed into a vacuum chamber where aluminum was vapor deposited at thicknesses well above the skin depth, e.g. 20-60 nm. The substrate was then placed in a magnetic field of ~1000 Oe. The particles were removed from the substrate via a small damp paintbrush. The paintbrush was sonicated in a small amount of water, typically 100-400 µL, where the particles could then be further diluted with glycerol for the experiments listed below. The particles fabricated in this way were used in Section 4.1, 4.2, and 4.3. A major drawback to this method is that the commercial magnetic particles have a high degree of sphere-to-sphere nonuniformity in both size and content of magnetic material (Häfeli et al., European Cells and Materials 3 (2002) 24-27).

3.1.2. Preparation of Uniform Half-Shell Particles

To improve uniformity over the commercial spheres described in Section 3.1.1, uniform magnetic half-shell particles were formulated (McNaughton et al., arXiv:cond-mat/0506418 (2005). 1.86 µm silica microspheres (Bangs Labs Fishers, Ind.) were dispersed into a monolayer on a glass substrate by spreading the manufacturer's stock solution of spheres over an area of a ~1.0 cm² and spin coating the slide. Varying layers and thicknesses of metal were then coated onto the spheres, in the following order: 6 nm of silver, 90 nm of iron, and 6 nm of silver. Spheres were then removed and suspended as described in Section 3.3.1 and used for the experiments discussed in Section 4.4. and 4.5.

3.2. Magnetic Rotation

All particles were observed in ~100 µm thick fluidic cells. Rotation was carried out with a digital function generator used to rotate a stepper motor connected to a 1.6 cm diameter diametrically magnetized Alnico magnet (Dexter Magnetics, Inc.). The magnet was placed in a horizontal orientation above the sample of interest at distances of 4-10 cm. This distance produced magnetic field values on the order of ~5-20 Oe. The particle under study was observed to be actively rotated by this external rotation field, and since no translation was observed, any magnetic gradient forces produced by the external field were negligible. Also, with the setup used in the experiments, no significant gradient is expected over the microdomain of one particle.

3.3. Microscopy

All microscopic images used to measure half-shell intensity or reflection were obtained with a Roper Coolsnap ES CCD camera (Roper Scientific Tucson, Ariz.) connected to an inverted epifluorescence microscope (Olympus, Center Valley, Pa.) in various configurations. The microscope was either operated in fluorescence mode, with the appropriate fluorescence filter cube, or in reflection mode, with a 50% reflection/50% transmission cube. In both cases a Xenon lamp was used either for reflection or to excite fluorescence of the particles. To observe the particles, a 60× (NA=0.85) objective lens was used in all experiments except binding detection and surface viscosity experiments, where a 100× (NA=1.25) immersion lens was used. Scanning electron microscopy images of the dried particles were obtained for characterization using a Phillips XL30 field emission gun.

3.4. Image Acquisition and Analysis

All images were acquired and analyzed using Metamorph software (Universal Imaging Corp, Sunnyvale, Calif.). Metamorph's ability to measure intensities of pixels of designated regions of interest was used to measure the time-dependant intensity or reflection from individual particles. A fluorescent particle will have one intensity peak per rotation but a particle monitored using reflection will have two intensity peaks per rotation. This dual peak behavior is a result of the light reflecting off both the convex and concave side of the metallic coating. The intensity expresses a sine-like dependence on the angle of the particle, thus making it possible to monitor the orientation of the particle. A fast Fourier transform was applied to the intensity time series to obtain the average rotation rate. Average rotation rates were obtained at varying frequencies of the external rotation rate. Finally, a least squares fit was used to fit Equation 8 to experimental results. This was the analysis method used in Section 4.1 and 4.6. Alternatively, with the measurement of a single average rotation rate at external driving frequencies $\Omega > \Omega_c$, the techniques described in Section 2.5 can be used to calculate the critical slipping rate. This was the analysis method used in Sections 4.2-4.5.

3.5. Temperature Control and Monitoring

The particles prepared in section 3.3.1 were suspended in a 0.95 glycerol-water mass fraction. This solution was placed in a sealed homemade fluidic cell that contained a T-type thermocouple. The error in temperature measurements were ±1° C. All thermocouple readings were taken when the magnetic field was not rotating to eliminate the effects of currents induced in the leads by the changing field. In this experiment and analysis, kinematic viscosity was used rather than dynamic viscosity because it has been reported that many of the dynamic viscosity tables are not accurate (Shankar et al., supra). All other sections report viscosity as dynamic as is the convention with phase-slipping experiments.

3.6. Particle Binding Experiments

In Section 4.4, the association and dissociation of a Dynal MyOne 1.0 µm paramagnetic bead with a 1.86 µm half-shell particle (preparation discussed in Section 3.1.2.) is described. The association of the 1.0 µm and the 1.86 µm half-shell particle was possible due to small magnetic interactions, while dissociation was performed using radiation pressure from a focused near-infrared Ti:Sapphire (Spectra Physics, Mountain View, Calif.) laser beam operating in continuous wave mode. Dissociation was induced by applying a 30 ms pulse of the focused light to the point of contact between the particles. The interference pattern of the beam reflected off the bottom glass surface of the fluidic cell, was also used to determine the approximate depth of the particles in the cell. This allowed for reproducibility measurements as seen in Section 4.4. Optical filters were used to block the reflected near-infrared light from reaching the CCD camera.

C. Results and Discussion

The linear-to-nonlinear rotation of magnetic particles rotated by an external driving field has a large variety of applications. All applications presented here involve calculation of the critical slipping rate, determined either by fitting a series of measurements at different external rotation rates as outlined in Section 3.4 or by calculating the critical rate from a single nonlinear rotation measurement as outlined in Section 2.5. These two methods are similar except that the fitting method has reduced error because more measurements are made to determine $\Omega_c$.

4. 1. Measurement of Magnetic Field

To demonstrate a nonlinear magnetic micro-oscillator's rotational dependence on external magnetic field strength, the magnitude of the magnetic field was changed and the critical slipping rate was measured. This was accomplished by increasing the distance between a rotating magnet and the sample plane. Solving for B in Equation 11 yields $$B = \frac{\kappa \eta V \Omega_c}{m} \quad (21)$$

Thus, the magnetic field is proportional to the critical slipping rate ($B \propto \Omega_c$). It is preferred that the magnetic field be rotating at a constant angular rate and be immersed in a fluid. It is in these situations—where local rotational fields or rotational fields on small dimensions are of interest—that application of critical phase-slipping for measurement of magnetic are particularly suited. The external magnetic field strength was changed from 87 Oe to 30 Oe, and accordingly the critical slipping rate changed from 5.81 rad/s to 2.15 rad/s. This change is to within 7.3% of that expected from Equation 21. While in this experiment the critical slipping rate was determined by means of a least squares fit, it is also possible to perform near real-time measurements on a changing magnetic field, by measuring the average rotation rate, namely $$B_2 = \frac{B_1 \Omega_c(B_2)}{\Omega_c(B_1)} = B_1 \left[ \frac{\langle \dot{\theta} \rangle_{B_2}}{\langle \dot{\theta} \rangle_{B_1}} \right]^{\frac{1}{2}} \left[ \frac{2\Omega - \langle \dot{\theta} \rangle_{B_2}}{2\Omega - \langle \dot{\theta} \rangle_{B_1}} \right]^{\frac{1}{2}}. \quad (22)$$

4.2. Measurement of Inter-Particle Magnetic Moment Uniformity

In general, magnetic microspheres have found many uses in biomedical applications, and in these applications the microspheres' magnetic characteristics are important (Connolly et al., Bio-Medical Materials and Engineering 15 (2005) 421-43 1). In particular, the type of magnetism, i.e. paramgnetism, superparamagnetism, or ferromagnetism, that the particles exhibit (Connolly et al., supra) and their uniformity of magnetic responsiveness (Häfeli et al., supra). The magnetic moment of microspheres that rotate in response to an externally rotating magnetic field can be determined by measuring the critical slipping rate. As with magnetic fields, the magnetic moment is proportional to the critical slipping rate, namely $$m = \frac{\kappa \eta V \Omega_c}{B} \quad (23)$$

Ultimately, this enables the measurement of the magnetic moment of single magnetic nanoparticles and microspheres. If the parameters in Equation 23 such as B, κ, V, or η cannot be determined, then the variation in the critical slipping rate will provide an estimation of the variation of the magnetic responsiveness rather than determining a value for m.

Several techniques have emerged to measure single particle and ensemble magnetic moments and magnetic responsiveness. Häfeli et al (supra),using a technique other than described here, have shown that commercially available magnetic particles vary in their magnetophoretic response from 30% -80%. Uniformity measurements were performed for the particles described in section 3.1.1 and 3.1.2. The half-shell reflection particles made by vapor deposition, described in section 3.1.2, had a variation in their magnetic responsiveness, i.e. standard deviation, of ~16%. Commercially obtained particles had a variation in magnetic responsiveness of ~50%, which is consistent with Häfeli's results. These values were measured through the nonlinear rotation of the half-shell particles. Generally, the magnetic moments of micro and nanoparticles are determined from ensemble measurements, where an average value for the magnetic moment is determined for the ensemble. Korneva and colleagues (Korneva et al., Nano Lett. 5 (2005) 879-884) used critical slipping to estimate the moment of magnetically loaded carbon nanotubes, but also monitored many particles at once, i.e. an ensemble value. In contrast, determining the critical slipping rate for individual particles, however, allows one to determine single particle magnetic moments and magnetic uniformity of an ensemble of particles.

4.3. Measurement of Viscosity

In a viscous fluid, measurement of $\Omega_c$ allows for the measurement of properties like the dynamic viscosity:

$$\eta = \frac{mB}{\kappa V \Omega_c} \quad (24)$$

If all of the microparticles have the same shape, volume, and magnetic content, it would be possible to measure a spatial distribution of viscosity. This ability can applied to complex fluids where pores of various sizes and spacings are present. By using these spatially resolved viscometers, the effective viscosity at various points in the complex fluid can be measured. Thus, this technique may be a useful addition to the growing list of colloidal probes used for microrheology (Waigh, Rep. Prog. Phys. 68 (2005) 685-742).

Using a single probe, it is possible to perform viscosity experiments. For example, the viscosity of glycerol has an exponential dependence on temperature, see Equation 19. The critical slipping rate for a single magnetic particle can be monitored while the temperature in a glycerol solution is altered. From Equation 20, it is clear that the critical slipping rate and, therefore, the nonlinear rotation rate of a rotationally driven microprobe can be used to determine viscosity as long as the starting viscosity is known.

Such an application was demonstrated by rotating particles in a 0.95 glycerol mass fraction solution and increasing the temperature of the glycerol-water mixture. The nonlinear rotation rate changes with temperature, increasing as temperature is increased. With this type of measurement one can calibrate the nonlinear rotation rate versus viscosity. By combining this technique with optical tweezers, it is possible to manipulate the magnetic particle (Agayan et al., Proceedings of SPIE 5514 (2004) 502-513, Merkt et al., arXiv:cond-mat/0605463 (2006)), after viscosity calibration, in more interesting systems like biological environments or near fluid-solid or fluid-air interfaces. From the work of Shankar (supra) it is possible to compare the experimental $\nu(T)$ with their reported $\nu(T)$. Table II shows this comparison, where the various viscosities were calculated using Equation 20. All calculated viscosity values had less than an 8% discrepancy from reported values.

4.4. Measurement of Binding Dynamics

Of all the variables in the critical slipping equation, volume is particularly significant. This significance is more apparent when considering a sphere. Substituting the volume of a sphere and a sphere's shape factor of 6 into Equation 16

$$\Omega_c = \frac{mB}{8\pi r_h^3}, \quad (25)$$

where $r_h$ is the hydrodynamic radius. Equation 25 indicates that $\Omega_c$ strongly depends on the radius of the rotating particle system. The effective shape and volume of the system can be changed by attachment to other objects such as other magnetic particles or biological agents like bacteria, viruses or proteins (See Example 1 above).

The ability to detect biological particles has become a highly pursued field of study and much attention has been directed toward nanoelectromechanical (NEMs) and other microscale oscillators (Ekinci et al., Review of Scientific Instruments 76 (2005) 061101; Fennimore et al., Nat. 424 (2003) 408).

These oscillators are cantilevers that have a natural oscillation frequency that changes when a biological agent binds to their functionalized surface. In this way, single bioparticles have been detected (Ilic et al., Journal of Vacuum Science & Technology B: Microelectronics and Nanometer Structures 19 (2001) 2825, Ilic et al., Appl. Phys. Lett. 85 (2004) 2604). While NEMs are very effective at detecting biological agents in vacuum or in air, they have not been applied to continuous monitoring in fluids. In air or in vacuum environments cantilever-based systems are extremely sensitive to physical changes (Verbridge et al., J. Appl. Phys. 99 (2006) 124304); however, due to viscous losses, this sensitivity decreases drastically when cantilevers are operated in fluids (Bhiladvala et al., Physical Review E 69 (2004) 36307, Paul et al., Phys. Rev. Lett. 92 (2004) 235501, Vignola et al., Applied Physics Letters 88 (2006) 041921).

Due to the deterministic behavior of a nonlinear rotating magnetic particle (see Equation 18), $\Omega_c$ can be calculated with the measurement of only one nonlinear rotation rate. For example, $\Omega_c$ was calculated with single average rotation rates at external rates of $\Omega > \Omega_c$ and the average difference between the value of $\Omega_c$ determined from a least-squares fit (as described in Section 3.4) and that determined from one value of $\langle \dot{\theta} \rangle$ was found to be only ~1.4%. Such low errors allow for accurate measurement of $\Omega_c$ which translates to more accurate measurement of the changes in drag of a single particle before and after a binding event. In the case of a paramagnetic particle binding to a half-shell particle, used to simulate a biological agent, where changes in m of the system are negligible, $$\frac{\Omega_{c1}}{\Omega_{c2}} = \frac{\frac{mB}{\eta \kappa_1 V_1}}{\frac{mB}{\eta \kappa_2 V_2}} = \frac{\kappa_2 V_2}{\kappa_1 V_1} \quad (26)$$

$$\Rightarrow \frac{\kappa_2 V_2}{\kappa_1 V_1} = \left[ \frac{\langle \dot{\theta}_1 \rangle}{\langle \dot{\theta}_2 \rangle} \right]^{\frac{1}{2}} \left[ \frac{2\Omega - \langle \dot{\theta}_1 \rangle}{2\Omega - \langle \dot{\theta}_2 \rangle} \right]^{\frac{1}{2}} \quad (27)$$

The first term on the right hand side of Equation 27 is the dominating factor, especially for large external rotation rates ($\Omega \gg \langle \dot{\theta}_1 \rangle > \langle \dot{\theta}_2 \rangle$). The second term acts as a correction factor that approaches unity as 1

$$1 + O\left( \frac{\langle \dot{\theta}_1 \rangle}{\Omega}, \frac{\langle \dot{\theta}_2 \rangle}{\Omega} \right).$$

Using the procedure described above, the changes in the volume and shape were monitored, when a 1.0 µm paramagnetic particle was bound to a 1.89 µm magnetic half-shell particle, by measuring the change in the average nonlinear rotation rate. This change, where the average rotation rate shifts from ~0.44 rot/s before binding to ~0.1 rot/s after binding, was measured with a measurement error of ~2%. These measurements were reproducible. Between measurements the system was either manipulated with a Ti:Sapphire laser beam (see Section 3.6) to dissociate the particles, or left alone to allow the particles to reattach. Equation 27 also allows for the approximation of the volume of the paramagnetic particle. From the rotational values ~0.44 rot/s and ~0.1 rot/s, the approximated diameter of the bound sphere was found to be ~1.08 µm and the estimated diameter from scanning electron microscopy was 1.01 µm. Thus, the capability of using this system to measure drag changes caused by a foreign object attaching to the micro-oscillator's surface has been demonstrated.

4.5. Estimation of Shape Factor

It is possible to use the nonlinear rotation of magnetic particles to measure the shape factor, $\kappa$. To calculate the effect of a shape factor change, one needs to double the magnetic moment and the volume of the micro-system. These two changes will have a canceling effect. If the original particles shape is known, then $\kappa_1$ will be well defined, e.g. for a sphere it would be 6. With this value, and measurement of the two critical slipping rates, $\kappa_2$ can be found from the relationship $$\kappa_2 = \kappa_1 \frac{\Omega_c(\kappa_1)}{\Omega_c(\kappa_2)} \quad (28)$$

This measurement was performed for two 1.86 µm half-shell particles binding to each other and found the value for $\kappa_2$ for the two-sphere system to be ~17. This value is between the shape factor for a sphere, which is 6, and that of a system of three spheres, which is 44 (Biswal et al., Anal. Chem. 76 (2004) 6448-6455).

4.6. Physiochemical Sensor

Combining the techniques and methods thus far described with chemical sensing probes yields a powerful physiochemical sensor (Bao et al., Nat. Mat. 2 (2003) 715-725). By measuring the nonlinear rotation of a magnetic particle, one can measure all of the physical properties discussed herein. Then, through the use of a fluorescent indicator dye located within the particle, or some equivalent synergistic scheme, local chemical concentrations can be measured. Such a probe is useful in elucidating the interplay between physical and chemical properties in live biological embryos or cells. It is also possible to add the physical probing capabilities to chemical sensors in a one step fabrication process, such as vapor deposition of magnetic materials (McNaughton et al., arXiv:cond-mat/0506418 (2005) ).

Example 4

Nonlinear Rotation Dynamics of Magnetic Microspheres With and Without Bacterium Attached Rotation rates were observed under fluorescent, reflection, and bright-field microscopy. FIG. 4(a) was obtained by measuring the average rotation rate of a magnetic microsphere (with an attached *E. coli*) for increasing magnetic driving frequencies. The critical frequency, where the magnetic particle goes from synchronous with driving field to asynchronous (nonlinear), occurs abruptly at 1.27 Hz. Measurements for (b), (c), and (d) were then made in this nonlinear regime. Bacteria attached to magnetic microspheres were optically detected by fluorescence of DsRed fluorescent protein transformed bacteria.

Figure 4:
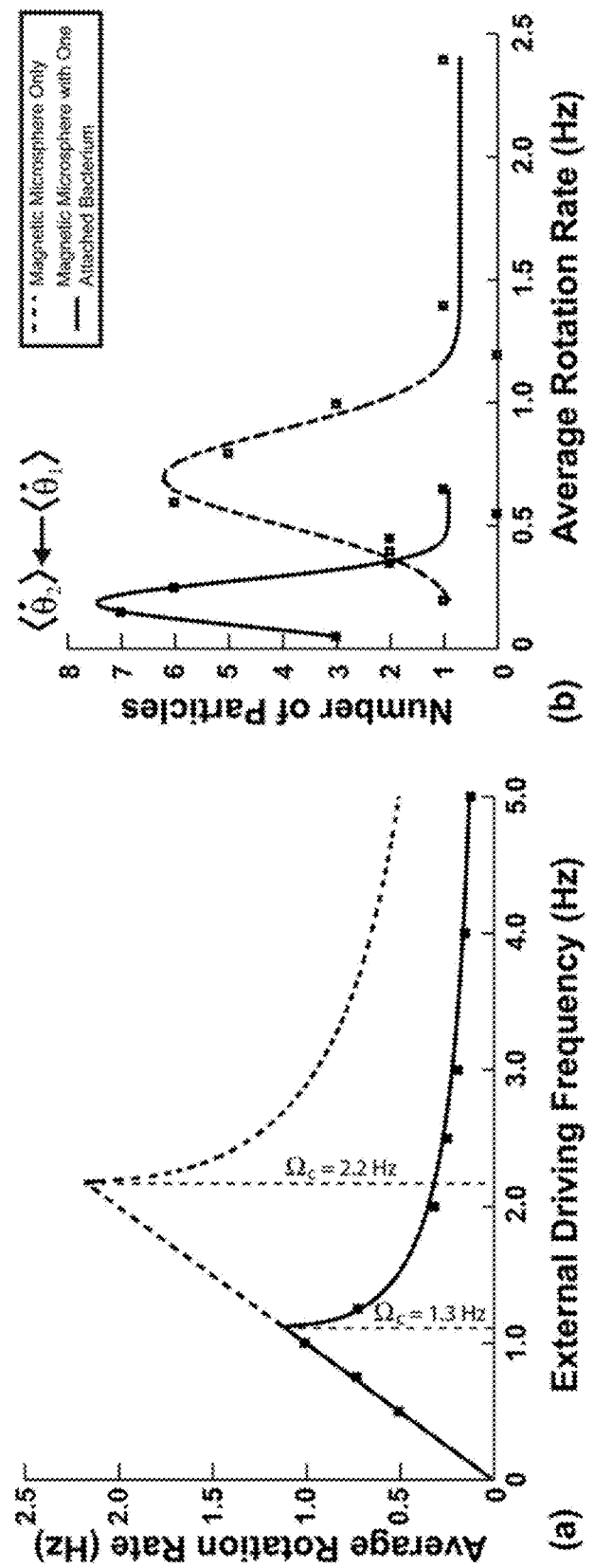
FIG. 4 shows rotation of magnetic particles with bacteria attached.
Figure 4:
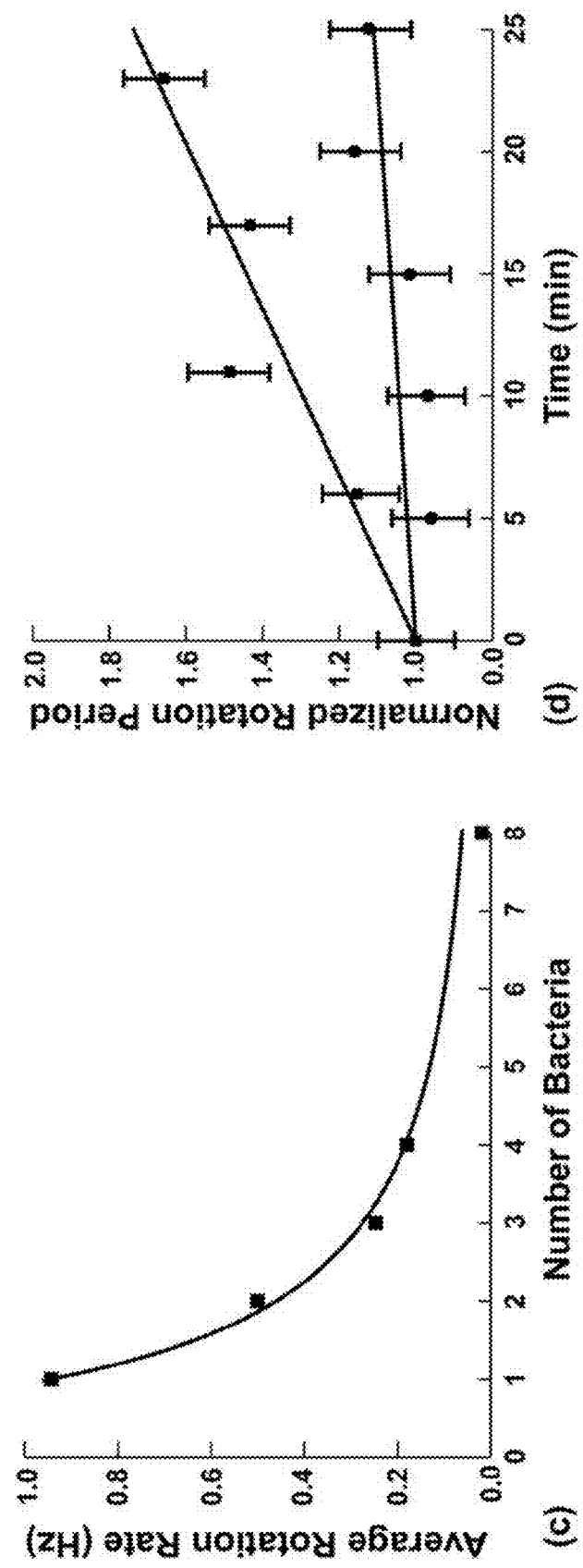

Results are shown in FIG. 4. FIG. 4a shows the rotational response of a single magnetic particle with one attached bacterium at various external driving frequencies, where the squares are data and the line is a theoretical fit for a particle with a bacterium attached (solid curve) and for one without (dashed curve). FIG. 4b shows the average nonlinear rotation frequency shift of 20 particles for single bacterium attachment. The magnetic microspheres with one bacterium attached rotated 33.8 times slower than the blank microspheres. FIG. 4c shows the change in nonlinear rotation rate as single bacterial cells sequentially attached to a single magnetic particle. FIG. 4d shows the change in normalized period resulting from growth of attached bacteria in a Luria-Bertani growth media (squares). There was an incremental 75% increase in rotation period over 25 min. A control was performed by exposing bacteria to isopropyl alcohol (70%) for 15 minutes (circles), giving an increase just within the limits of the error bars.

Figure 5:
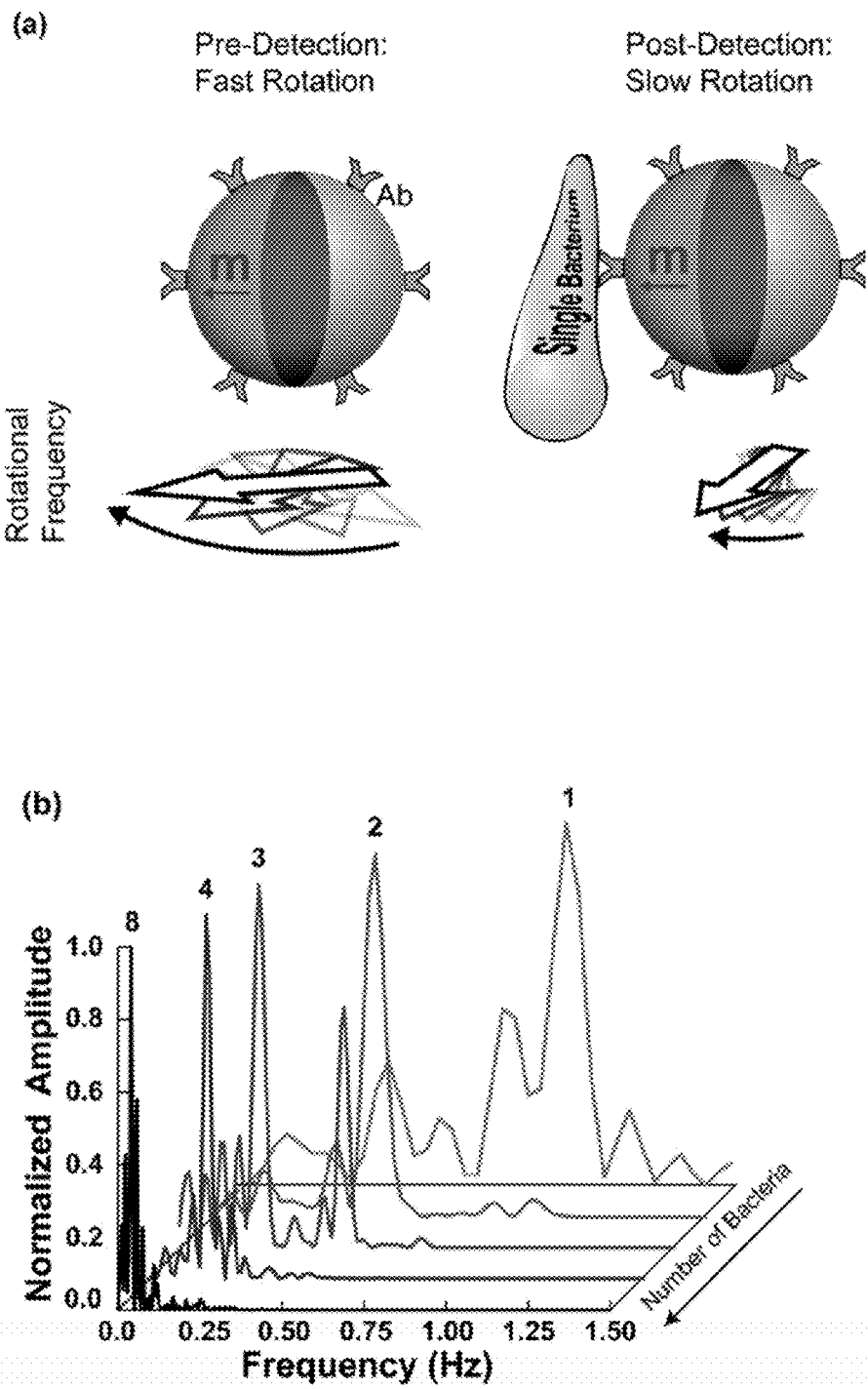
FIG. 5 shows rotating magnetic microspheres bound to bacteria.

FIG. 5 shows rotating magnetic microspheres bound to bacteria. FIG. 5a shows a schematic of the asynchronous (nonlinear) rotation changes that a magnetic microsphere undergoes when bound to a bacterium (e.g., the rotational frequency is reduced). The magnetic microspheres are functionalized with an antibody that specifically binds to the bacterial strain of interest. FIG. 5b shows the power spectral density of a rotating magnetic microsphere dimer driven at 3.75 Hz, where 1, 2, 3, 4, and 8 bacterial cells were sequentially attached.

Example 5

Detection Device

This example describes an exemplary device for detection of non-linear rotation. FIG. 6 shows one example of the hardware's configuration. The device is simple and utilizes inexpensive components (i.e. it utilizes similar components as a CD-ROM). The laser in the device is focused so that the size of the beam is smaller than the particle. This allows for the entire beam to be blocked or passed, depending on the orientation of the particle being monitored, which maximizes the signal change.

A label is used to amplify the change in the rotation rate. When a biological agent attaches to a rotating magnet it causes a change in drag. This change in drag is amplified through the attachment of a sphere or some other body (label). This amplification causes a nonlinear rotating particle to go from linear to nonlinear (synchronous to asynchronous).

Figure 8:
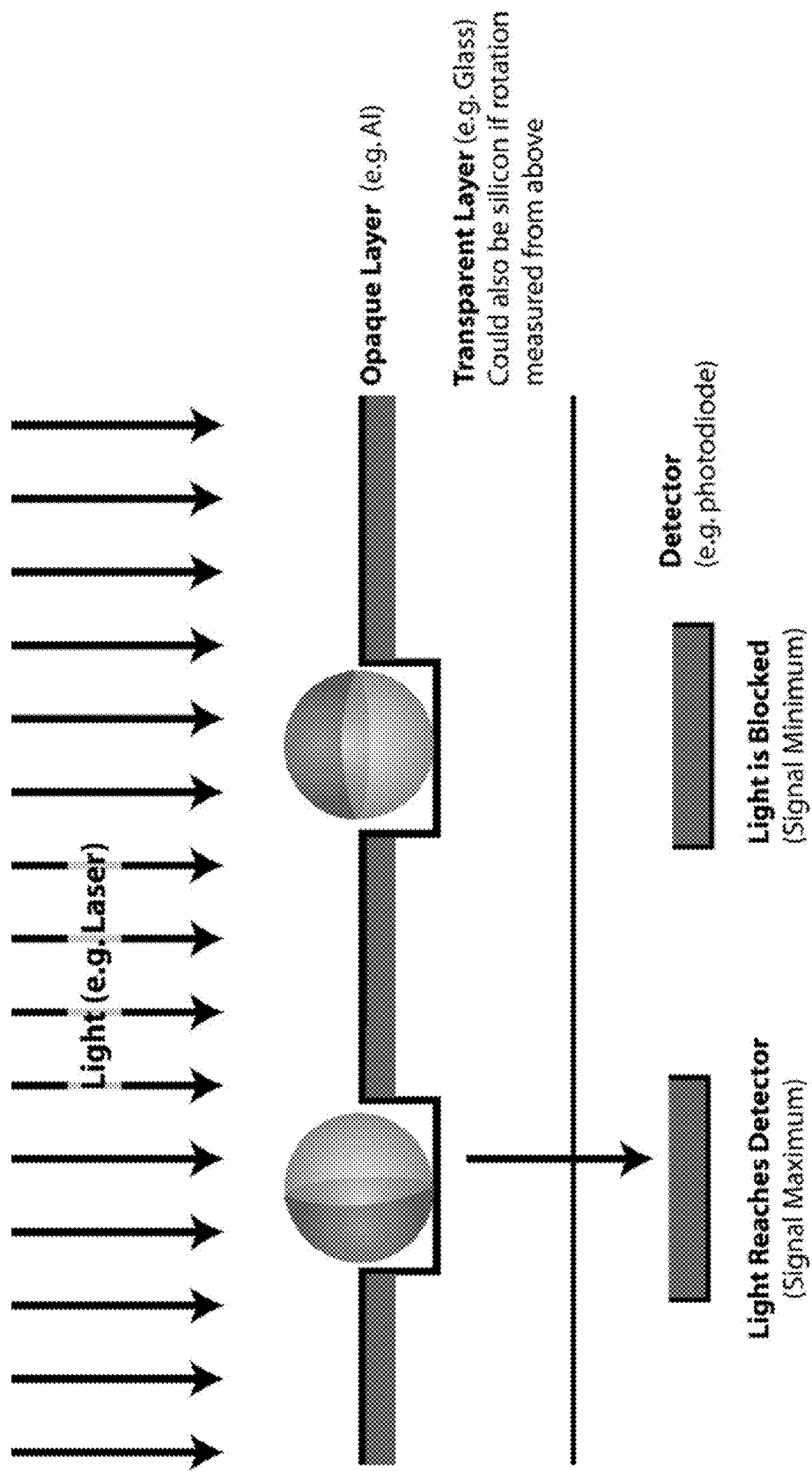
FIG. 8 shows a schematic depicting how a micro-fabricated fluidic chip interfaces to a device, where the spheres are functionalized with pathogen specific antibodies.

An array of magnetic microspheres in microwells where only the light near or above the wells is passed through to the photodiodes (or camera) is used (FIG. 8). This allows for the light fluctuations caused by the particles to be observed without a focusing lens. This maximizes the signal changes created by the rotating particles.

Example 6

Effect of Antibiotic on Cell Growth

FIG. 9 shows the normalized rotational period of a small cluster of 40 μm magnetic particles. The top curve is for several particles attached to a small colony of *E. coli* K-12 bacteria in Luria Broth (Miller) Growth Media. The rotational period increases over time, indicating bacterial grow. This data is compared to the bottom curve, where bacteria and particles have been exposed to 5% w/v Ampicillin antibiotic solution. In this case, the rotational period decreases or stays constant over time, indicating that the antibiotic is working to stop bacterial growth.

In certain configurations, especially when particles are at an interface, such as an air-liquid interface, the nonlinear rotation may occur in a plane perpendicular to the plane of the external driving magnetic field. This type of nonlinear rotation occurred in the above exemplary measurement.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of detecting the presence of an analyte in a sample, comprising:
   contacting a magnetic particle with said sample under conditions such that said particle interacts with said analyte;
   rotating said magnetic particle using an external rotating magnetic field applied to the sample;
   measuring the non-linear rotation rate of said magnetic particle during application of the rotating magnetic field; and
   determining the presence of said analyte in said sample when said non-linear rotation rate is altered relative to a rotational rate of the magnetic particle in the absence of said sample.

2. The method of claim 1, wherein said analyte is a cell.

3. The method of claim 2, wherein said particle further comprises a ligand that specifically binds to said cell.

4. The method of claim 3, wherein said ligand is an antibody.

5. The method of claim 2, further comprising:
   determining growth in cell population in said sample over a sampling time period, by measuring changes in the non-linear rotation rate of said magnetic particle over time.

6. The method of claim 2, wherein said cell is a microorganism.

7. The method of claim 6, wherein said microorganism is a bacteria.

8. The method of claim 1, further comprising the step of contacting said sample with a label that binds to said analyte, wherein the rotation rate of said particle is altered when said label is bound to said analyte.

9. The method of claim 1, wherein the magnetic particle is a ferromagnetic particle.

10. The method of claim 1, wherein the magnetic particle is a paramagnetic particle.

11. The method of claim 1, wherein rotating said magnetic particle using the external rotating magnetic field comprises maintaining the external rotating magnetic field at a single driving frequency.

12. The method of claim 1, wherein rotating said magnetic particle using the external rotating magnetic field comprises maintaining the external rotating magnetic field above a critical driving frequency.

13. The method of claim 1, further comprising:
   determining a critical driving frequency for the rotating magnetic field, where the critical driving frequency depends upon particle volume, viscosity, magnetic moment, a magnetic field amplitude; and
   applying the external rotating magnetic field to the sample at a driving frequency above the critical driving frequency.

14. The method of claim 1, wherein the external rotating magnetic field is supplied by pairs of Helmholtz coils producing the rotating magnetic field in a plane.

15. The method of claim 1, wherein measuring the non-linear rotation rate of said magnetic particle and determining the presence of said analyte in said sample comprises:
   illuminating the magnetic particle and analyte with an light source; and
   detecting a resulting optical signal from the illuminated magnetic particle, where the optical signal varies with the non-linear rotation rate.

16. The method of claim 15, wherein detecting the optical signal comprises collecting the optical signal using a photodiode apparatus.

17. The method of claim 15, wherein detecting the optical signal comprises collecting the optical signal using a charged coupled device or camera.

18. The method of claim 15, wherein detecting the optical signal comprises collecting the optical signal using a fluorescence detection apparatus.

19. The method of claim 15, wherein the magnetic particle is rotating in a plane perpendicular to a sample plane of a detection apparatus.

20. The method of claim 15, wherein the magnetic particle is rotating in a plane parallel to a sample plane of a detection apparatus.

21. The method of claim 1, wherein measuring the non-linear rotation rate of said magnetic particle and determining the presence of said analyte in said sample comprises passively monitoring the non-linear rotation rate.

22. The method of claim 1, wherein the analyte comprises a cell and a virus.

23. The method of claim 1, wherein the analyte comprises a virus.

24. The method of claim 1, wherein the analyte comprises a biological molecule.

25. A method for measuring changes in the number and/or size of cells bound to magnetic particles, the method comprising:
   contacting magnetic particles with a solution comprising cells under conditions such that said magnetic particles bind to said cells;
   rotating said magnetic particles using an external rotating magnetic field; and
   during application of the rotating magnetic field, measuring changes in the non-linear rotation rate of said magnetic particles over time, wherein said non-linear rotation rate is altered in response to change in the number and/or size of said cells bound to said magnetic particles.

26. The method of claim 25, wherein said cells comprise microorganisms.

27. The method of claim 25, wherein the magnetic particle is a ferromagnetic particle.

28. The method of claim 25, wherein the magnetic particle is a paramagnetic particle.

29. The method of claim 25, wherein rotating said magnetic particles comprises maintaining the external rotating magnetic field at a single driving frequency.

30. The method of claim 25, wherein rotating said magnetic particles comprises maintaining the external rotating magnetic field above a critical driving frequency.

31. The method of claim 25, further comprising determining growth in the number of said cells bound to said magnetic particles.

* * * * *